US009737256B2

(12) United States Patent
Chen et al.

(10) Patent No.: US 9,737,256 B2
(45) Date of Patent: Aug. 22, 2017

(54) APPARATUS AND METHODS FOR NON-INVASIVE ASSESSMENT OF TRANSPLANT KIDNEY VIABILITY

(71) Applicants: University of Maryland, College Park, MD (US); Georgetown University, Washington, DC (US)

(72) Inventors: Yu Chen, Rockville, MD (US); Hsing-Wen Wang, Arlington, VA (US); Peter Andrews, McLean, VA (US); Jeremiah Wierwille, New Knoxville, OH (US)

(73) Assignees: University of Maryland, College Park, MD (US); Georgetown University, Washington, DC (US)

( * ) Notice: Subject to any disclaimer, the term of this patent is extended or adjusted under 35 U.S.C. 154(b) by 240 days.

(21) Appl. No.: 14/581,295

(22) Filed: Dec. 23, 2014

(65) Prior Publication Data

US 2015/0201878 A1    Jul. 23, 2015

Related U.S. Application Data

(60) Provisional application No. 61/920,072, filed on Dec. 23, 2013.

(51) Int. Cl.
*A61B 5/05* (2006.01)
*A61B 5/20* (2006.01)
(Continued)

(52) U.S. Cl.
CPC .............. *A61B 5/201* (2013.01); *A61B 5/004* (2013.01); *A61B 5/0066* (2013.01);
(Continued)

(58) Field of Classification Search
CPC .......... A61B 5/055; A61B 5/201; A61B 5/417
See application file for complete search history.

(56) References Cited

U.S. PATENT DOCUMENTS 7,146,204 B2 * 12/2006 Degani ................. A61B 5/055
600/410

OTHER PUBLICATIONS

F. van Bel, G.L. Guit, J. Schipper, M. van de Bor, and J. Baan, Indomethacin-induced changes in renal blood flow velocity waveform in premature infants investigated with color Doppler imaging. J Pediatr, 118(4 Pt 1): p. 621-6 (1991).

(Continued)

*Primary Examiner* — Joel Lamprecht
(74) *Attorney, Agent, or Firm* — Carter, DeLuca, Farrell & Schmidt, LLP

(57) ABSTRACT

A kidney viability assessment system (KVAS) is disclosed which provides objective and reliable tests to assess the viability of transplant or donor kidneys in vivo and predict their post-transplant outcomes. KVAS includes an optical device augmented by an intelligent algorithm that can evaluate the viability or quality of the donor kidney in a real-time, non-invasive way. In particular, it includes a handheld optical coherence tomography (OCT) imaging device and at least one processor configured for executing a set of instructions corresponding to an automatic image processing algorithm for quantification of kidney microstructures and functions. Handheld OCT can survey the entire surface of kidney, and the image processing algorithm automatically segments and quantifies the diameter and/or density of the kidney microstructures, blood flows, etc., and quantitative values are displayed in real-time on a display of the KVAS.

19 Claims, 20 Drawing Sheets

(51) Int. Cl.
A61B 5/00 (2006.01)
A61B 5/026 (2006.01)
A61B 5/107 (2006.01)

(52) U.S. Cl.
CPC .......... *A61B 5/0261* (2013.01); *A61B 5/1079* (2013.01); *A61B 5/413* (2013.01); *A61B 2505/05* (2013.01); *A61B 2576/02* (2013.01)

(56) References Cited

OTHER PUBLICATIONS

S.N. Wong, R.N. Lo, and E.C. Yu, Renal blood flow pattern by noninvasive Doppler ultrasound in normal children and acute renal failure patients. J Ultrasound Med, 8(3): p. 135-41 (1989).
T. Yura, S. Yuasa, M. Fukunaga, K.F. Badr, and H. Matsuo, Role for Doppler ultrasound in the assessment of renal circulation: effects of dopamine and dobutamine on renal hemodynamics in humans. Nephron, 71(2): p. 168-75 (1995).
K. Kalantarinia, J.T. Belcik, J.T. Patrie, and K. Wei, Real-time measurement of renal blood flow in healthy subjects using contrast-enhanced ultrasound. American Journal of Physiology-Renal Physiology, 297(4): p. F1129-F1134 (2009).
D.H. Kay, M. Mazonakis, C. Geddes, and G. Baxter, Ultrasonic microbubble contrast agents and the transplant kidney. Clin Radio, 64(11): p. 1081-7 (2009).
P.M. Andrews, W.M. Petroll, H.D. Cavanagh, and J.V. Jester, Tandem scanning confocal microscopy (TSCM) of normal and ischemic living kidneys. Am J Anat, 191(1): p. 95-102 (1991).
V. Yang, M. Gordon, B. Qi, J. Pekar, S. Lo, E. Seng-Yue, A. Mok, B. Wilson, and I. Vitkin, High speed, wide velocity dynamic range Doppler optical coherence tomography (Part I): System design, signal processing, and performance. Opt Express, 11(7): p. 794-809 (2003).
S. Yazdanfar, A.M. Rollins, and J.A. Izatt, Imaging and velocimetry of the human retinal circulation with color Doppler optical coherence tomography. Opt Lett, 25(19): p. 1448-50 (2000).
L. Yu and Z. Chen, Doppler variance imaging for three-dimensional retina and choroid angiography. J Biomed Opt, 15 (1): p. 016029-1 to 016029-4 (2010).
Y. Wang, B.A. Bower, J.A. Izatt, O. Tan, and D. Huang, Retinal blood flow measurement by circumpapillary Fourier domain Doppler optical coherence tomography. J Biomed Opt, 13(6): p. 064003-1 to 064003-9 (2008).
R.M. Werkmeister, N. Dragostinoff, M. Pircher, E. Gotzinger, C.K. Hitzenberger, R.A. Leitgeb, and L. Schmetterer, Bidirectional Doppler Fourier-domain optical coherence tomography for measurement of absolute flow velocities in human retinal vessels. Opt Lett, 33(24): p. 2967-9 (2008).
J. Barton, J.A Izatt M.D. Kulkarni, S. Yazdanfar, and A.J. Welch, Three-dimensional reconstruction of blood vessels from in vivo color Doppler optical coherence tomography images. Dermatology, 198(4): p. 355-61 (1999).
Y. Zhao, Z. Chen, C. Saxer, Q. Shen, S. Xiang, J.F. de Boer, and J.S. Nelson, Doppler standard deviation imaging for clinical monitoring of in vivo human skin blood flow. Opt Lett, 25(18): p. 1358-60 (2000).
H. Li, B.A. Standish, A. Mariampillai, N.R. Munce, Y. Mao, S. Chiu, N.E. Marcon, B.C. Wilson, A. Vitkin, and V.X.D. Yang, Feasibility of interstitial Doppler optical coherence tomography for in vivo detection of microvascular changes during photodynamic therapy. Lasers Surg Med, 38(8): p. 754-61 (2006).
V.X.D. Yang, S.J. Tang, M.L. Gordon, B. Qi, G. Gardiner, M. Cirocco, P. Kortan, G.B. Haber, G. Kandel, I.A. Vitkin, B.C. Wilson, and N.E. Marcon, Endoscopic Doppler optical coherence tomography in the human GI tract: initial experience. Gastrointest Endosc, 61(7): p. 879-90 (2005).
W.M. Stahl, Effect of Mannitol on the Kidney: Changes in Intrarenal Hemodynamics. N Engl J Med, 272: p. 382-6 (1965).

K.E. Lindstrom, L. Ronnstedt, G. Jaremko, and B. Haraldsson, Physiological and morphological effects of perfusing isolated rat kidneys with hyperosmolal mannitol solutions. Acta Physiol Scand, 166(3): p. 231-8 (1999).
R. Behnia, E. Koushanpour, and E.A. Brunner, Effects of hyperosmotic mannitol infusion on hemodynamics of dog kidney. Anesth Analg, 82(5): p. 902-8 (1996).
X. Deng, W.J. Welch, and C.S. Wilcox, Role of nitric oxide in short-term and prolonged effects of angiotensin II on renal hemodynamics. Hypertension, 27(5): p. 1173-9 (1996).
L. Ekelund and J. Gothlin, Effect of angiotensin on normal renal circulation determined by angiography and a dye dilution technique. Acta Radiol Diagn (Stockh), 18(1): p. 39-48 (1977).
J.H. Gothlin, J. Krakenes, and S. Tvete, The effects of angiotensin on the diagnostics and haemodynamics in renal angiography. Eur J Radiol, 3(4): p. 328-30 (1983).
J.E. Hall and J.P. Granger, Renal hemodynamic actions of angiotensin II: interaction with tubuloglomerular feedback. Am J Physiol, 245(2): p. R166-73 (1983).
K.M. Denton, W.P. Anderson, and R. Sinniah, Effects of angiotensin II on regional afferent and efferent arteriole dimensions and the glomerular pole. Am J Physiol Regul Integr Comp Physiol, 279(2): p. R629-38 (2000).
V.J. Srinivasan, S. Sakadzic, I. Gorczynska, S. Ruvinskaya, W. Wu, J.G. Fujimoto, and D.A. Boas, Quantitative cerebral blood flow with optical coherence tomography. Opt Express, 18(3): p. 2477-94 (2010).
Q. Li, M.L. Onozato, P.M. Andrews, C.W. Chen, A. Paek, R. Naphas, S. Yuan, J. Jiang, A. Cable, and Y. Chen, Automated quantification of microstructural dimensions of the human kidney using optical coherence tomography (OCT). Opt Express, 17(18): p. 16000-16 (2009).
M.L. Onozato, P.M. Andrews, Q. Li, J. Jiang, A. Cable, and Y. Chen, Optical coherence tomography of human kidney. J Urol, 183(5): p. 2090-4 (2010).
V. Jayaraman, J. Jiang, H. Li, P.J.S. Heim, G.D. Cole, B. Potsaid, J.G. Fujimoto, and A. Cable, OCT Imaging up to 760 kHz Axial Scan Rate using Single-Mode 1310nm MEMS-Tunable VCSELs with >100nmTuning Range, in Conference on Lasers and Electro-Optics: Applications and Technology 2011, Optical Society of America: Baltimore, MD. p. PDPB2.pdf-2 pages.
A. Agrawal, M. Connors, A. Beylin, C.P. Liang, D. Barton, Y. Chen, R.A. Drezek, and T.J. Pfefer, Characterizing the point spread function of retinal OCT devices with a model eye-based phantom. Biomed Opt Express, 3(5): p. 1116-26 (2012).
A. Ahmad, S.G. Adie, E.J. Chaney, U. Sharma, and S.A. Boppart, Cross-correlation-based image acquisition technique for manually-scanned optical coherence tomography. Opt Express, 17(10): p. 8125-36 (2009).
P.M. Andrews and S.B. Bates, Improving Euro-Collins flushing solution's ability to protect kidneys from normothermic ischema. Miner Electrolyte Metab, 11(5): p. 309-13 (1985).
P.M. Andrews and S.B. Bates, Dietary protein prior to renal ischemia dramatically affects postischemic kidney function. Kidney Int, 30(3): p. 299-303 (1986).
C.W. Chen, M.W. Betz, J.P. Fisher, A. Paek, and Y. Chen, Macroporous hydrogel scaffolds and their characterization by optical coherence tomography. Tissue Engineering: Part C, 17: p. 101-112 (2011).
X. Qi, Y.S. Pan, Z.L. Hu, W. Kang, J.E. Willis, K. Olowe, M.V. Sivak, and A.M. Rollins, Automated quantification of colonic crypt morphology using integrated microscopy and optical coherence tomography. Journal of Biomedical Optics, 13(5): p. -054055-1 to 054055-11 (2008).
K. Zhang and J.U. Kang, Real-time intraoperative 4D full-range FD-OCT based on the dual graphics processing units architecture for microsurgery guidance. Biomed Opt Express, 2(4): p. 764-70 (2011).
K. Zhang and J.U. Kang, Graphics processing unit accelerated non-uniform fast Fourier transform for ultrahigh-speed, real-time Fourier-domain OCT. Opt Express, 18(22): p. 23472-87 (2011).

(56) References Cited

OTHER PUBLICATIONS

K. Zhang and J.U. Kang, Real-time 4D signal processing and visualization using graphics processing unit on a regular nonlinear-k Fourier-domain OCT system. Opt Express, 18(11): p. 11772-84 (2011).
C.B. Anderson and E.E. Etheredge, Human renal allograft blood flow and early renal function. Ann Surg, 186(5): p. 564-7 (1977).
H.B. Fang, G. Li, and J. Sun, Maximum likelihood estimation in a semiparametric proportional hazards cure model. Scandinavian Journal of Statistics, 32: p. 59-75 (2005).
Y. Chen, A.D. Aguirre, P. Hsiung, S.W. Huang, H. Mashimo, J.M. Schmitt, and J.G. Fujimoto, Effects of Axial Resolution Improvement on Optical Coherence Tomography (OCT) Imaging of Gastrointestinal Tissues. Optics Express, 16: p. 2469-2485 (2008).
P.M. Andrews and K.R. Porter, A scanning electron microscopic study of the nephron. Am J Anat, 140(1): p. 81-115 (1974).
United States Renal Data System Annual Data Report, (2009) pp. 1-412.
F. Sanfilippo, W.K. Vaughn, E.K. Spees, and B.A. Lucas, The detrimental effects of delayed graft function in cadaver donor renal transplantation. Transplantation, 38(6): p. 643-8 (1984).
M. Szostek, R. Danielewicz, B. Lagiewska, M. Pacholczyk, Z. Rybicki, G. Michalak, L. Adadynski, J. Walaszewski, and W. Rowinski, Successful transplantation of kidneys harvested from cadaver donors at 71 to 259 minutes following cardiac arrest. Transplant Proc, 27(5): p. 2901-2 (1995).
J. Light, Viability testing in the non-heart-beating donor. Transplant Proc, 32(1): p. 179-81 (2000).
A.B. Maunsbach, The influence of different fixatives and fixation methods on the ultrastructure of rat kidney proximal tubule cells. I. Comparison of different perfusion fixation methods and of glutaraldehyde, formaldehyde and osmium tetroxide fixatives. J Ultrastruct Res, 15(3): p. 242-82 (1966).
P.M. Andrews, Noninvasive vital microscopy to monitor tubular necrosis of cold-stored kidneys. Transplantation, 57(8): p. 1143-8 (1994).
P.M. Andrews, B.S. Khirabadi, and B.C. Bengs, Using tandem scanning confocal microscopy to predict the status of donor kidneys. Nephron, 91(1): p. 148-55 (2002).
V. Campo-Ruiz, G.Y. Lauwers, R.R. Anderson, E. Delgado-Baeza, and S. Gonzalez, Novel virtual biopsy of the kidney with near infrared, reflectance confocal microscopy: a pilot study in vivo and ex vivo. J Urol, 175(1): p. 327-36 (2006).
J.J. Kang, I. Toma, A. Sipos, F. McCulloch, and J. Peti-Peterdi, Quantitative imaging of basic functions in renal (patho) physiology. Am J Physiol Renal Physiol, 291(2): p. F495-502 (2006).
K. Dunn, R. Sandoval, K. Kelly, P.C. Dagher, G.A. Tanner, S.J. Atkinson, R.L. Bacallao, and B.A. Molitoris, Functional studies of the kidney of living animals using multicolor two-photon microscopy. Am J Physiol Cell Physiol, 283(3): p. C905-16 (2002).
W. Yu, R.M. Sandoval, and B.A. Molitoris, Rapid determination of renal filtration function using an optical ratiometric imaging approach. Am J Physiol Renal Physiol, 292(6): p. F1873-80 (2007).
D. Huang, E.A. Swanson, C.P. Lin, J.S. Schuman, W.G. Stinson, W. Chang, M.R. Hee, T. Flotte, K. Gregory, C.A. Puliafito, and J.G. Fujimoto, Optical coherence tomography. Science, 254(5035): p. 1178-1181 (1991).
J.G. Fujimoto, Optical coherence tomography for ultrahigh resolution in vivo imaging. Nature Biotechnology, 21(11): p. 1361-1367 (2003).
M.R. Hee, J.A. Izatt, E.A. Swanson, D. Huang, J.S. Schuman, C.P. Lin, C.A. Puliafito, and J.G. Fujimoto, Optical coherence tomography of the human retina. Archives of Ophthalmology, 113(3): p. 325-332 (1995).
C.A. Puliafito, M.R. Hee, J.S. Schuman, and J.G. Fujimoto, Optical coherence tomography of ocular diseasesThorofare, NJ: Slack Inc., pp. 1-367 and Index 2 pages (1996).
G. Wollstein, L.A. Paunescu, T.H. Ko, J.G. Fujimoto, A. Kowalevicz, I. Hartl, S. Beaton, H. Ishikawa, C. Mattox, O. Singh, J. Duker, W. Drexler, and J.S. Schuman, Ultrahigh-resolution optical coherence tomography in glaucoma. Ophthalmology, 112(2): p. 229-37 (2005).
M. Brezinski, Characterizing arterial plaque with optical coherence tomography. Current opinion in cardiology, 17(6): p. 648-55 (2002).
I.K. Jang, B. Bouma, B. MacNeill, M. Takano, M. Shishkov, N. Iftima, and G.J. Tearney, In-vivo coronary plaque characteristics in patients with various clinical presentations using Optical Coherence Tomography. Circulation, 108 (17): p. 373-373 (2003).
B.E. Bouma, G.J. Tearney, C.C. Compton, and N.S. Nishioka, High-resolution imaging of the human esophagus and stomach vivo using optical coherence tomography. Gastrointestinal Endoscopy, 51: p. 467-74 (2000).
M.V. Sivak, Jr., K. Kobayashi, J.A. Izatt, A.M. Rollins, R. Ung-Runyawee, A. Chak, R.C. Wong, G.A. Isenberg, and J. Willis, High-resolution endoscopic imaging of the GI tract using optical coherence tomography. Gastrointestinal Endoscopy, 51: p. 474-9 (2000).
X.D. Li, S.A. Boppart, J. Van Dam, H. Mashimo, M. Mutinga, W. Drexler, M. Klein, C. Pitris, M.L. Krinsky, M.E. Brezinski, and J.G. Fujimoto, Optical coherence tomography: advanced technology for the endoscopic imaging of Barrett's esophagus. Endoscopy, 32(12): p. 921-30 (2000).
Y. Chen, A.D. Aguirre, P.L. Hsiung, S. Desai, P.R. Herz, M. Pedrosa, Q. Huang, M. Figueiredo, S.W. Huang, A. Koski, J.M. Schmitt, J.G. Fujimoto, and H. Mashimo, Ultrahigh resolution optical coherence tomography of Barrett's esophagus: preliminary descriptive clinical study correlating images with histology. Endoscopy, 39(7): p. 599-605 (2007).
J. Wetzel, E. Lankenau, R. Birngruber, and R. Engelhardt, Optical coherence tomography of the human skin. Journal of the American Academy of Dermatology, 37(6): p. 958-63 (1997).
L.L. Otis, M.J. Everett, U.S. Sathyam, and B.W. Colston, Jr., Optical coherence tomography: a new imaging technology for dentistry. The Journal of the American Dental Association, 131(4): p. 511-4 (2000).
A.V. D'Amico, M. Weinstein, X. Li, J.P. Richie, and J. Fujimoto, Optical coherence tomography as a method for identifying benign and malignant microscopic structures in the prostate gland. Urology, 55(5): p. 783-7 (2000).
C. Pitris, A. Goodman, S.A. Boppart, J.J. Libus, J.G. Fujimoto, and M.E. Brezinski, High-resolution imaging of gynecologic neoplasms using optical coherence tomography. Obstetrics and Gynecology, 93(1): p. 135-9 (1999).
G.J. Tearney, S.A. Boppart, B.E. Bouma, M.E. Brezinski, N.J. Weissman, J.F. Southern, and J.G. Fujimoto, Scanning single-mode fiber optic catheter-endoscope for optical coherence tomography. Optics Letters, 21(7): p. 543-5 (1996).
P.R. Herz, Y. Chen, A.D. Aguirre, J.G. Fujimoto, H. Mashimo, J. Schmitt, A. Koski, J. Goodnow, and C. Petersen, Ultrahigh resolution optical biopsy with endoscopic optical coherence tomography. Optics Express, 12(15): p. 3532-3542 (2004).
X. Li, C. Chudoba, T. Ko, C. Pitris, and J.G. Fujimoto, Imaging needle for optical coherence tomography. Optics Letters, 25(20): p. 1520-2 (2000).
Y. Chen, P.M. Andrews, A.D. Aguirre, J.M. Schmitt, and J.G. Fujimoto, High-resolution three-dimensional optical coherence tomography imaging of kidney microanatomy ex vivo. J Biomed Opt, 12(3): p. 034008-1 to 034008-7 (2007).
P.M. Andrews, Y. Chen, M.L. Onozato, S.W. Huang, D.C. Adler, R.A. Huber, J. Jiang, S.E. Barry, A.E. Cable, and J.G. Fujimoto, High-resolution optical coherence tomography imaging of the living kidney. Lab Invest, 88(4): p. 441-449 (2008).
J. Wierwille, P.M. Andrews, M.L. Onozato, J. Jiang, A. Cable, and Y. Chen, In vivo, label-free, three-dimensional quantitative imaging of kidney microcirculation using Doppler optical coherence tomography. Lab Invest, 91(11): p. 1596-1604 (2011).
T. Yamamoto, T. Tada, S.V. Brodsky, H. Tanaka, E. Noiri, F. Kajiya, and M.S. Goligorsky, Intravital videomicroscopy of peritubular capillaries in renal ischemia. Am J Physiol Renal Physiol, 282(6): p. F1150-F1155 (2002).
M. Angelescu, T. Kraus, M. Wiese, O. Hergesell, U. Haberkorn, and E. Klar, Assessment of renal graft function by perioperative moni-

(56) References Cited

OTHER PUBLICATIONS toring of cortical microcirculation in kidney transplantation. Transplantation, 75(8): p. 1190-6 (2003).

Y. Ogasawara, K. Takehara, T. Yamamoto, R. Hashimoto, H. Nakamoto, and F. Kajiya, Quantitative blood velocity mapping in glomerular capillaries by in vivo observation with an intravital videomicroscope. Methods Inf Med, 39(2): p. 175-8 (2000).

H.N. Ibrahim and T.H. Hostetter, Diabetic nephropathy. J Am Soc Nephrol, 8(3): p. 487-93 (1997).

G.T. O'Bryan and T.H. Hostetter, The renal hemodynamic basis of diabetic nephropathy. Semin Nephrol, 17(2): p. 93-100 (1997).

I. Ichikawa and A. Fogo, Focal segmental glomerulosclerosis. Pediatr Nephrol, 10(3): p. 374-91 (1996).

Z. Szabo, J. Xia, W.B. Mathews, and P.R. Brown, Future direction of renal positron emission tomography. Semin Nucl Med, 36(1): p. 36-50 (2006).

L. Juillard, M.F. Janier, D. Fouque, L. Cinotti, N. Maakel, D. Le Bars, P.Y. Barthez, N. Pozet, and M. Laville, Dynamic renal blood flow measurement by positron emission tomography in patients with CRF. Am J Kidney Dis, 40(5): p. 947-54 (2002).

N. Kudomi, N. Koivuviita, K.E. Liukko, V.J. Oikonen, T. Tolvanen, H. Iida, R. Tertti, K. Metsarinne, P. Iozzo, and P. Nuutila, Parametric renal blood flow imaging using [15O]H2O and PET. Eur J Nucl Med Mol Imaging, 36(4): p. 683-91 (2009).

E.U. Nitzsche, Y. Choi, D. Killion, C.K. Hoh, R.A. Hawkins, J.T. Rosenthal, D.B. Buxton, S.C. Huang, M.E. Phelps, and H.R. Schelbert, Quantification and parametric imaging of renal cortical blood flow in vivo based on Patlak graphical analysis. Kidney Int, 44(5): p. 985-96 (1993).

H.R. Middlekauff, E.U. Nitzsche, A.H. Nguyen, C.K. Hoh, and G.G. Gibbs, Modulation of renal cortical blood flow during static exercise in humans. Circ Res, 80(1): p. 62-8 (1997).

N.M. Alpert, C.A. Rabito, D.J. Correia, J.W. Babich, B.H. Littman, R.G. Tompkins, N.T. Rubin, R.N. Rubin, and A.J. Fischman, Mapping of local renal blood flow with PET and H(2)(15)O. J Nucl Med, 43(4): p. 470-5 (2002).

N. Michoux, X. Montet, A. Pechere, M.K. Ivancevic, P.Y. Martin, A. Keller, D. Didier, F. Terrier, and J.P. Vallee, Parametric and quantitative analysis of MR renographic curves for assessing the functional behaviour of the kidney. Eur J Radiol, 54(1): p. 124-35 (2005).

J.P. Vallee, F. Lazeyras, H.G. Khan, and F. Terrier, Absolute renal blood flow quantification by dynamic MRI and Gd-DTPA. Eur Radiol, 10(8): p. 1245-2 (2000).

L. Bokacheva, H. Rusinek, J.L. Zhang, and V.S. Lee, Assessment of renal function with dynamic contrast-enhanced MR imaging. Magn Reson Imaging Clin N Am, 16(4): p. 597-611, viii (2008).

C. De Bazelaire, N.M. Rofsky, G. Duhamel, M.D. Michaelson, D. George, and D.C. Alsop, Arterial spin labeling blood flow magnetic resonance imaging for the characterization of metastatic renal cell carcinoma(1). Acad Radiol, 12(3): p. 347-57 (2005).

H. Akinbi, S. Abbasi, P.L. Hilpert, and V.K. Bhutani, Gastrointestinal and renal blood flow velocity profile in neonates with birth asphyxia. J Pediatr, 125(4): p. 625-7 (1994).

\* cited by examiner

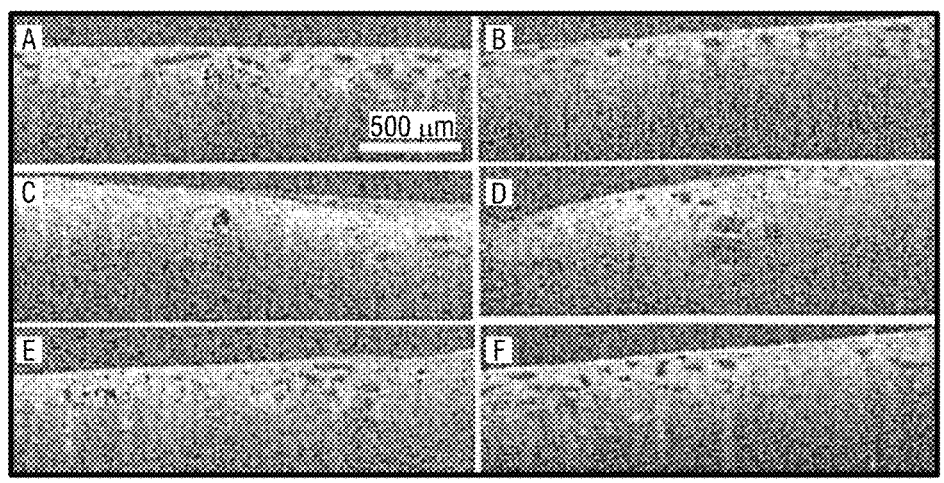
FIG. 17
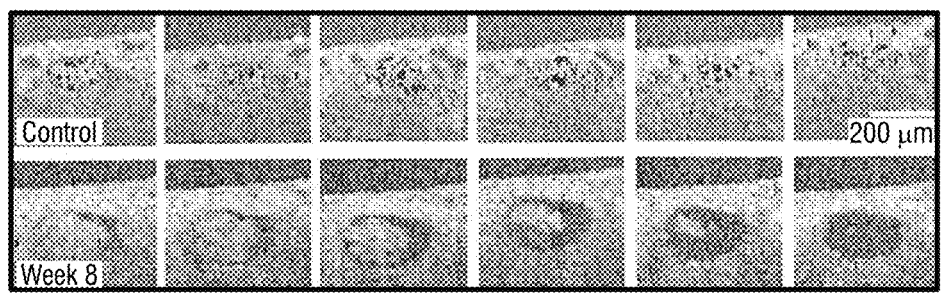
FIG. 18
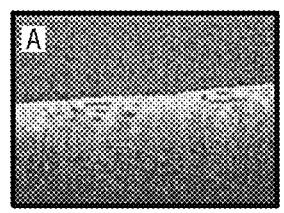 
FIG. 19A   FIG. 19B

APPARATUS AND METHODS FOR NON-INVASIVE ASSESSMENT OF TRANSPLANT KIDNEY VIABILITY

CROSS-REFERENCE TO RELATED APPLICATION AND PUBLICATIONS

This application claims the benefit of, and priority to, U.S. Provisional Patent Application No. 61/920,072, filed on Dec. 23, 2013, entitled "APPARATUS AND METHODS FOR NON-INVASIVE ASSESSMENT OF TRANSPLANT KIDNEY VIABILITY" by Yu Chen et al.; the entire contents of which are incorporated by reference herein. This application is related to Li et al., *Automated quantification of microstructural dimensions of the human kidney using optical coherence tomography (OCT)*, Optics Express, 17(18): p. 16000-16 (Aug. 25, 2009); the entire contents of which are incorporated by reference herein. This application is also related to Andrews et al., *Optical Coherence Tomography of the Living Human Kidney*, Journal of Innovative Optical Health Sciences, vol. 7, no. 2 (published on Dec. 10, 2013); the entire contents of which are incorporated by reference herein. This application is also related to Wang et al., *Optical Coherence Tomography Imaged Ischemic Insult During Kidney Transplant*, poster presentation at the Biomedical Engineering Society (BMES) Annual Meeting on Sep. 25, 2013; the entire contents of which are incorporated by reference herein.

BACKGROUND

1. Technical Field

The present disclosure relates to the field of Optical Coherence Tomography (OCT). More particularly, the present disclosure relates to apparatus and methods for non-invasive assessment of transplant kidney viability using OCT.

2. Background of Related Art

A. The Need for a Better Test to Predict Post-Transplant Renal Outcome

More than half a million US residents have end-stage renal disease (ESRD), which is associated with high mortality rates (157.3 deaths per 1,000 patient years) and a huge economic burden (more than $30 billion per year) [1]. The treatment options for ESRD include dialysis and kidney transplantation. Transplantation is the preferred option because it promises to extend the patients' lives and also improve their life quality. Currently, with over 77,500 patients annually waiting for kidney transplants, organ shortages pose a major problem in kidney transplantation. While the vast majority of kidneys used for transplantation are obtained from heart-beating cadavers, many kidneys available for transplant are not utilized because of their unknown status (i.e., from non-heart beating cadavers, long storage times, etc.).

Also, ischemic insult suffered by cadaver kidneys awaiting transplantation frequently causes acute tubular necrosis (ATN) leading to varying degrees of delayed graft function (DGF) after transplantation, which represents a significant risk for eventual graft and patient survival[2], and can be difficult to discern from rejection. The incidence of DGF is estimated to be 15-70% [3]. Unfortunately, in present clinical practice, there is no reliable test to determine the viability of donor kidneys and whether or not donor kidneys might exhibit DGF. A timely biochemical analysis of kidneys has proven disappointing with no biochemical criteria proving accurate[4]. Therefore, there is a critical need for objective and reliable tests to predict post-transplant outcome to use organs safely and utilize the donor pool optimally.

B. Non Invasive Imaging to Predict Post-Transplant Renal Outcome

Conventional light microscopy of excision kidney biopsies are not as useful to evaluate kidney pathology as non-invasive imaging procedures because of dramatic destructive artifacts to the kidney tubules associated with such biopsies [5]. In addition, unlike non-invasive imaging procedures, excision biopsies are destructive to kidneys, take time to analyze, and image only small segments of the kidney (i.e., cannot provide global imaging of numerous regions across the kidney surface). Previous studies by one of us (Andrews et al.) have shown that a non-invasive imaging technique termed tandem scanning confocal microscopy (TSCM) could be used to determine the degree of ATN by analyzing the superficial nephrons of living rabbit donor kidneys [6]. Using TSCM, Andrews et al. observed that the histopathological changes (e.g., ATN) of superficial proximal tubules of rabbit kidneys for transplant correlated closely with subsequent post-transplant renal function[7] (see FIGS. 1A-1F taken from Andrews et al., Nephron, 2002 [7]).

FIGS. 1A-1D show TSCM images of subcapsular proximal convoluted tubules of a rabbit kidney 1 hour (FIG. 1A), 24 hours (FIG. 1B), 48 hours (FIG. 1C) and 72 hours (FIG. 1D) following harvesting. With increasing storage time, TSCM images depict the degeneration of the superficial proximal tubules. FIG. 1E illustrates a summary of the serum creatinine (SCr) in mg/dL versus various days following transplantation and FIG. 1F illustrates a summary of blood urea nitrogen (BUN) values in mg/dL measured at various days post-transplantation. As the storage time increased the post-transplant SCr and BUN values increased. All the rabbits in the 24-, 48-, and 67-hour groups exhibited various degrees of DGF but eventually survived. SCr and BUN returned to normal values. All rabbits in the 72-hour group eventually died of uremia. This is not surprising in that the status of superficial proximal convoluted tubules is indicative of the status of proximal convoluted tubules throughout the entire kidney cortex.

Other investigators have also used near-infrared confocal microscopy [8] and multi-photon microscopy [9-11] to demonstrate the ability to perform non-invasive imaging of kidney structure and function in animal models. However, the maximum penetration depth associated with these microscopy procedures is limited (about 100 μm for TSCM), which makes it difficult to impossible to non-destructively image the human kidney using the foregoing non-invasive imaging microscopic techniques, especially if it is surrounded by an intact human renal capsule. Indeed, in a previous clinical trial, the inventors of the present application found that the limited penetrating ability of TSCM precluded them from imaging human donor kidneys even when an attempt was made to remove the renal capsule [unpublished observations]. Also, conventional bulky systems TSCM are awkward in orientating the kidney specimens and especially difficult when attempting to image the kidney in situ.

SUMMARY

The embodiments and methodologies of the present disclosure provide a novel and non-obvious solution to conventional systems and methods for non-invasive assessment of transplant kidney viability. A kidney viability assessment system (KVAS) is disclosed which provides objective and reliable tests to assess the viability of transplant or donor kidneys in vivo and predict their post-transplant outcomes. KVAS includes an optical device augmented by an intelligent algorithm that can evaluate the viability or quality of a donor kidney in a real-time, non-invasive way.

In particular, KVAS includes a handheld optical coherence tomography (OCT) imaging device and at least one processor configured for executing a set of instructions corresponding to an automatic image processing algorithm for quantification of kidney microstructures and functions. Previous research has demonstrated the morphology of kidney microstructures (such as, for example, tubular diameters and/or density) is closely correlated with subsequent post-transplant renal function. Handheld OCT can survey the entire surface of kidney, and the image processing algorithm of the present disclosure automatically segments and quantifies the diameter and/or density of the kidney microstructures, blood flows, etc., and quantitative values are displayed. The quantitative values can be displayed in real-time on a display of the KVAS.

In one exemplary embodiment according to the present disclosure, there is provided a system for non-invasive assessment of a transplant or donor kidney. The system includes an optical device for imaging the donor kidney in vivo and generating at least one image. The system further includes at least one processor configured for receiving the at least one image from the optical device. The at least one processor is further configured for executing a set of instructions corresponding to an algorithm for processing the at least one image and determining at least one characteristic corresponding to the viability of the donor kidney.

The at least one processor is also capable of predicting the donor kidney's post-transplant outcome. The system determines at least one characteristic corresponding to the viability of the donor kidney in real-time. The optical device is a handheld optical coherence tomography imaging device and is configured for surveying the entire surface of the donor kidney. The at least one characteristic is indicative of the donor kidney's microstructures and functions. The algorithm segments and quantifies the diameter and/or density of the donor kidney's microstructures and blood flows. The system further includes a display for displaying quantitative values corresponding to the donor kidney determined by the algorithm. The quantitative values can be displayed in real-time.

In another exemplary embodiment according to the present disclosure, there is provided a method for non-invasive assessment of a transplant or donor kidney. The method includes imaging the donor kidney in vivo and generating at least one image by an optical device; processing the at least one image; and determining at least one characteristic corresponding to the viability of the donor kidney. The method further includes the step of predicting the donor kidney's post-transplant outcome. The determining step determines the at least one characteristic corresponding to the viability of the donor kidney in real-time.

The optical device is a handheld optical coherence tomography imaging device. The at least one characteristic is indicative of the donor kidney's microstructures and functions. The optical device is configured for surveying the entire surface of the donor kidney. The processing step includes segmenting and quantifying the diameter and/or density of the donor kidney's microstructures and blood flows. The method further includes displaying quantitative values corresponding to the donor kidney. The quantitative values can be displayed by a display in real-time.

In still another exemplary embodiment according to the present disclosure, there is provided a computer-readable medium storing a set of instructions configured for being executed by at least one processor for performing a method for non-invasive assessment of a transplant or donor kidney. The method includes imaging the donor kidney in vivo and generating at least one image by an optical device; processing the at least one image; and determining at least one characteristic corresponding to the viability of the donor kidney.

BRIEF DESCRIPTION OF THE DRAWINGS

The above-mentioned advantages and other advantages will become more apparent from the following detailed description of the various exemplary embodiments of the present disclosure with reference to the drawings wherein:

FIG. 17 shows images A-F of OCT/DOCT imaging showing the blood flow, glomerulus, and tubules in rat kidneys wherein images A-F are cross-sectional OCT/DOCT images of normal (images A and B) and diseased rat kidneys after Adriamycin-induced CKD at week 2 (images C and D) and week 3 (images E and F);

FIG. 18 illustrates an upper row of images of the kidney of a control animal for different cross-sections across a single glomerulus ranging from Y=0 μm, Y=15 μm, Y=30 μm, Y=45 μm, Y=60 μm, and Y=75 μm and a lower row of images of the kidney of the glomerulus at Week 8 of a CDK animal at the same cross-sections across a single glomerulus showing that increased Bowman's space and decreased blood flow were seen in the glomerulus of week 8 CDK animal, indicating glomerulosclerosis;

FIG. 19A shows an example OCT image of a rat kidney with tubular opening percentage of 29%;

FIG. 19B is an image segmentation algorithm to quantify the opening areas within the ROI (from the surface to 177 μm below the surface);

DETAILED DESCRIPTION

Figures 1A, 1B, 1C, 1D:
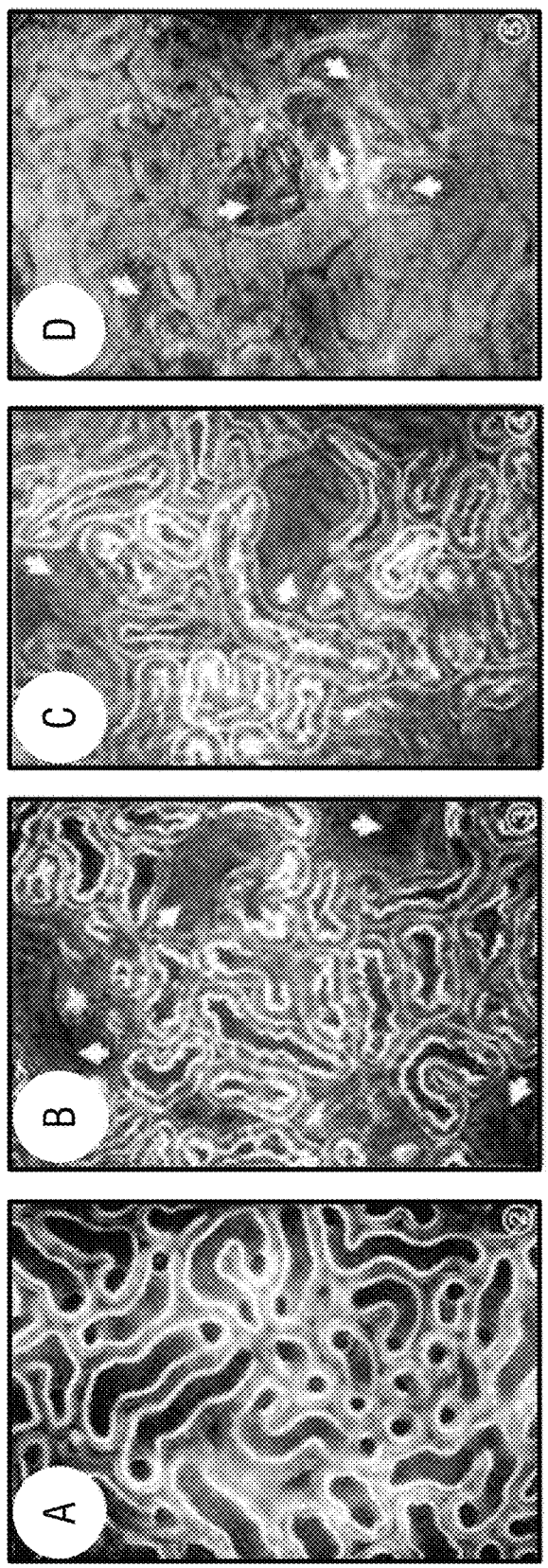
FIG. 1A shows a TSCM image of subcapsular proximal convoluted tubules of a rabbit kidney 1 hour following harvesting according to the prior art.
FIG. 1B shows a TSCM image of subcapsular proximal convoluted tubules of a rabbit kidney 24 hours following harvesting according to the prior art.
FIG. 1C shows a TSCM image of subcapsular proximal convoluted tubules of a rabbit kidney 48 hours following harvesting according to the prior art.
FIG. 1D shows a TSCM image of subcapsular proximal convoluted tubules of a rabbit kidney 72 hours following harvesting according to the prior art.
Figure 1E:
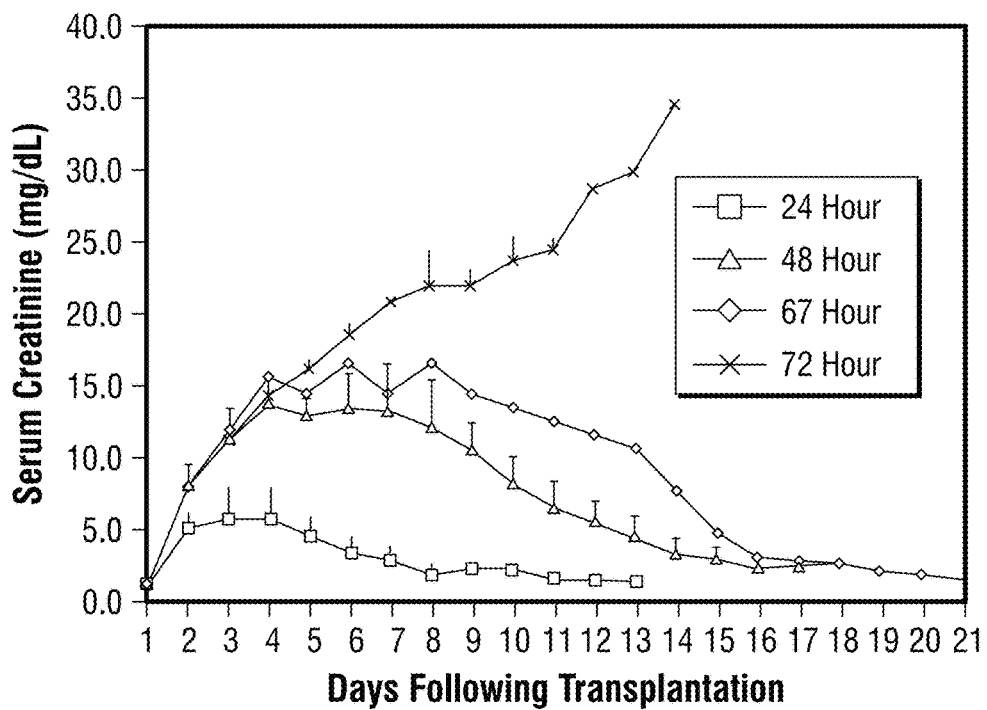
FIG. 1E shows a summary of serum creantine (SCr) versus days following transplantation according to the prior art.
Figure 1F:
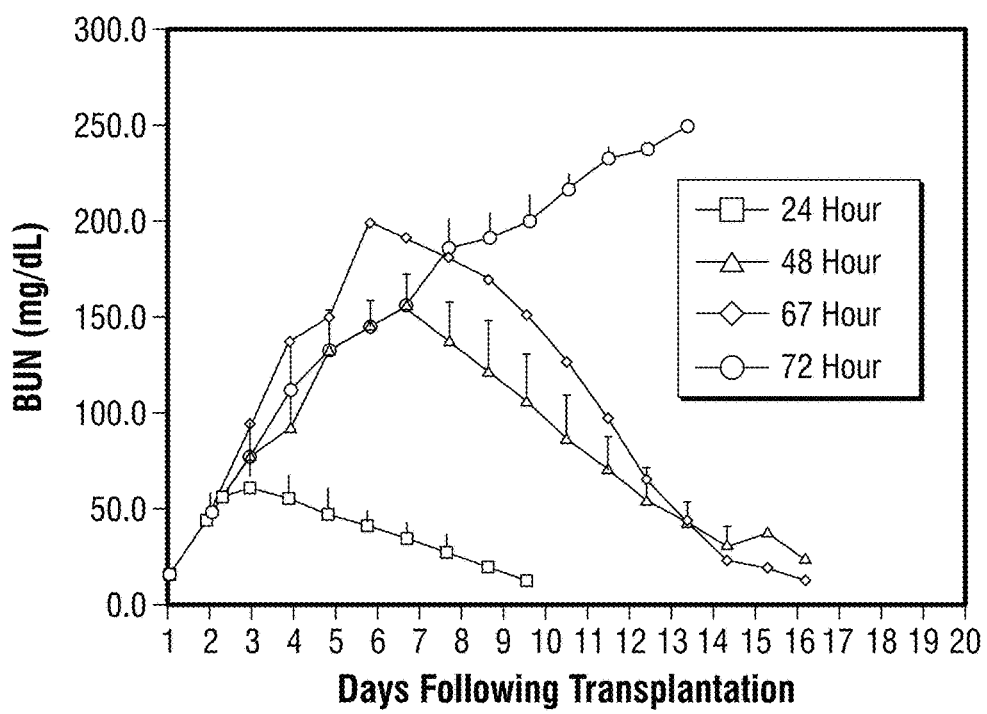
FIG. 1F shows a summary of blood urea nitrogen versus days following transplantation according to the prior art.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The word "exemplary" is used herein to mean "serving as an example, instance, or illustration." Any embodiment described herein as "exemplary" is not necessarily to be construed as preferred or advantageous over other embodiments.

It is to be understood that the method steps described herein and claimed in the claim below need not necessarily be performed in the order as described. Further, words such as "thereafter," "then," "next," etc., are not intended to limit the order of the steps. These words are simply used to guide the reader through the description of the method steps.

The implementations described herein may be implemented in, for example, a method or a process, an apparatus, a software program, a data stream, or a signal. Even if only discussed in the context of a single form of implementation (for example, discussed only as a method), the implementation of features discussed may also be implemented in other forms (for example, an apparatus or program). An apparatus may be implemented in, for example, appropriate hardware, software, and firmware. The methods may be implemented in, for example, an apparatus such as, for example, a processor, which refers to processing devices in general, including, for example, a computer, a microprocessor, an integrated circuit, or a programmable logic device. Processors also include communication devices, such as, for example, computers, cell phones, tablets, portable/personal digital assistants, and other devices that facilitate communication of information between end-users within a network.

The general features and aspects of the present disclosure remain generally consistent regardless of the particular purpose. Further, the features and aspects of the present disclosure may be implemented in system in any suitable fashion, e.g., via the hardware and software configuration of system or using any other suitable software, firmware, and/or hardware. For instance, when implemented via executable instructions, such as the set of instructions, various elements of the present disclosure are in essence the code defining the operations of such various elements. The executable instructions or code may be obtained from a computer-readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

According to the present disclosure a kidney viability assessment system (KVAS) is disclosed which provides objective and reliable tests to assess the viability of donor kidneys and predict their post-transplant outcomes. KVAS includes an optical device augmented by an intelligent algorithm that can evaluate the viability or quality of a donor kidney in a real-time, non-invasive way. The algorithm includes a set of instructions (i.e., executable instructions) configured for being executed by at least one processor of the KVAS.

In particular, KVAS includes a handheld optical coherence tomography (OCT) imaging device and at least one processor configured for executing a set of instructions corresponding to an automatic image processing algorithm for quantification of kidney microstructures and functions. Previous research has demonstrated the morphology of kidney microstructures (such as tubular diameters and/or density) is closely correlated with subsequent post-transplant renal function. Handheld OCT can survey the entire surface of kidney, and the image processing algorithm automatically segments and quantifies the diameter and/or density of the kidney microstructures, blood flows, etc., and quantitative values are displayed. The quantitative values can be displayed in real-time on a display of the KVAS.

In the following sections, advantages of KVAS for non-invasive imaging and image processing for evaluating transplant kidneys are described; previous studies using OCT to evaluate kidney function; and preliminary results using OCT/DOCT (Doppler OCT) to evaluate transplant kidneys. The preliminary results suggest that KVAS using OCT/DOCT can provide novel and vital intra-operative monitoring and evaluation of the transplant kidney for predicting post-renal function.

I. Advantages of Optical Coherence Tomography (OCT) as a Non-Invasive Imaging Procedure to Evaluate the Transplant Kidneys OCT is a rapidly emerging imaging modality that can function as a type of "optical biopsy", providing cross-sectional images of tissue morphology in situ and in real-time [12, 13]. OCT is similar to ultrasound imaging, except that it uses the echo delay of light instead of sound to generate images. OCT is safer than X-ray technologies, much less expensive than MRI devices, and provides higher resolution images than ultrasound. By employing broadband optical light sources, OCT can achieve axial resolutions of 1-10 μm, more than an order of magnitude above that obtainable for clinical ultrasound. As a result, OCT can provide very high-resolution images of organs and tissues in a non-invasive manner. This potential has been demonstrated in a number of biomedical applications including ophthalmology [14-16], cardiology [17, 18], gastroenterology [19-22], dermatology [23], dentistry [24], urology [25] and gynecology [26], among others.

In contrast to other forms of non-invasive light microscopy, OCT can image with longer working distances, improved penetration depth and without the need for tissue contact. Not only can it image up to depths of ~1-2 mm in most light-scattering tissues, OCT can also provide three-dimensional images in arbitrary planes. Finally, OCT can be performed using a thin flexible sterile endoscope or catheter [27, 28] or even with a needle [29], enabling ease of use and the possibility of imaging deep within a solid tissue or organ. To make OCT more applicable to the clinical situation, the co-inventors herein developed a handheld OCT unit that has proven highly effective in our preliminary clinical trials. OCT has proven especially valuable in studying the living kidney because not only are excisional biopsies invasive, damaging and can only sample a very small region of the kidney, they also produce severe artifacts that are difficult to distinguish from ischemia and other injuries.

In preliminary clinical investigations, the co-inventors herein have provided evidence demonstrating OCT's capability for imaging intact human kidney microstructures both ex vivo and in vivo (i.e., following transplant into patient). Since the morphology of superficial proximal tubules correlates very well with post-transplantation renal function[7], the information obtained by OCT could be useful to evaluate the donor kidney status.

II. Previous Studies

A. OCT Studies of the Kidney Using a Rat Model

Initially, two of the co-inventors herein investigated the ability of OCT to provided clinically relevant information using a rat kidney model [30]. Two of the co-inventors herein subsequently studied the capability of using OCT to monitor kidney structural changes in response to ischemic insult in the living rat (i.e., in vivo) [31]. A laparotomy was performed on the anesthetized animal and the living kidneys exposed for in situ observation. The co-inventors observed the kidneys prior to, during, and following exposure to renal ischemia induced by clamping the renal artery. Again, OCT enabled visualization of the morphology of both uriniferous tubules and renal glomeruli. When renal ischemia was induced, OCT revealed dramatic shrinkage of tubular lumens due to the swelling of the epithelial lining [31]. Total occlusion of the tubule lumens occurred within a minute following onset of ischemia. 3D segmentation provided an estimation of changes in the total tubular volumes in response to ischemia [31]. Pre-treatment with intravenous mannitol (1.0 ml of 25% mannitol solution) protected the tubules from ischemic induced swelling. These observations demonstrated that OCT represents an exciting new approach to visualize renal histopathological changes in vivo.

B. Non Invasive Imaging of Renal Microcirculation Using Doppler OCT (DOCT)

Three of the co-inventors herein have demonstrated that OCT can be used in a Doppler mode (DOCT) to image microvascular blood flow in the kidney [32]. This is an additional parameter to measure in kidney transplantation, in view of studies indicating that blood perfusion may be correlated with both intermediate and long-term graft function[33, 34]. Also, intrarenal hemodynamic abnormalities are thought to be a primary factor associated with the onset and progression of acute injury [35], as well as diabetic nephropathy [36, 37], and focal segmental glomerulosclerosis (FSGS) [38]. Real-time assessment of renal morphological and hemodynamic changes could therefore help to evaluate the kidney condition and offer valuable information to predict the prognosis of injury or disease, lending to the development of patient-specific management strategies.

There is no sensitive and objective tool for clinical monitoring of renal microcirculatory changes. In the past, renal blood flow (RBF) has been monitored using a number of different imaging modalities including positron emission tomography (PET) [39-44], magnetic resonance angiography (MRA) [45-48], Doppler ultrasound (US) [49-52] and contrast-enhanced ultrasound (CE-US) [53, 54]. While these techniques allow for non-invasive, wide field-of-view (FOV) imaging, they do not have sufficient resolution to detect changes in renal microcirculation. Optical imaging techniques that have higher resolutions and greater sensitivities could be a more feasible method for monitoring and evaluating microcirculatory changes, especially in an intra-operative setting. Studies using confocal [7, 8, 55] and multi-photon microscopy [9-11] have demonstrated the ability to image kidney microstructure and function (blood flow and filtration rate) in animal glomerular capillaries. However, again the penetration depth has been limited to several-hundred microns, and they require the need to administer contrast agents to determine flow. Therefore, using these imaging modalities for human studies pose certain challenges due to the capsule surrounding the human kidney, which can be several-hundred microns thick, and the need to inject contrast agents into the patient.

OCT and its functional extension DOCT are emerging imaging technologies that have the capacity to provide real-time imaging of tissue in a non-invasive fashion with high-resolution near that of conventional histopathology. DOCT can be used to visualize blood flow non-invasively by measuring the Doppler frequency shifts in the OCT interference signal caused by moving scatterers that are label-free, such as red blood cells [56]. DOCT has been used to image and quantify blood flow in vivo for multiple clinical applications including retina [57-60], skin [61-63], and gastrointestinal tract [64], among others.

In one study, the co-inventors herein investigated the feasibility of DOCT to image kidney microcirculation, specifically, glomerular blood flow. DOCT is able to capture 3D data sets consisting of a series of cross-sectional images in real-time, which enables label-free and non-invasive quantification of glomerular blood flow. The kidneys of adult, male Munich-Wistar rats were exposed through laparotomy procedure after being anesthetized. Following exposure of the rat kidney beneath the OCT/DOCT microscope, glomerular blood flow was observed as shown in FIG. 2 (from [32]).

Images A, D, G represent OCT en face views of a single glomerulus. B, E, H represent Doppler optical coherence tomography (DOCT) en face view of the same imaging plane. Images C, F, I represent fused OCT/DOCT image showing spatial agreement between the OCT image and the corresponding DOCT image. The three images in each row correspond to the same imaging plane. Depth (A-C)=440 µm; (B-F)=470 µm; (G-I)=545 µm. OCT/DOCT provides virtual sectioning of the glomerulus. The arrow in H represents the vascular pole (i.e., afferent/efferent arterioles). Image size: 325×278 µm. From [32].

Figure 2:
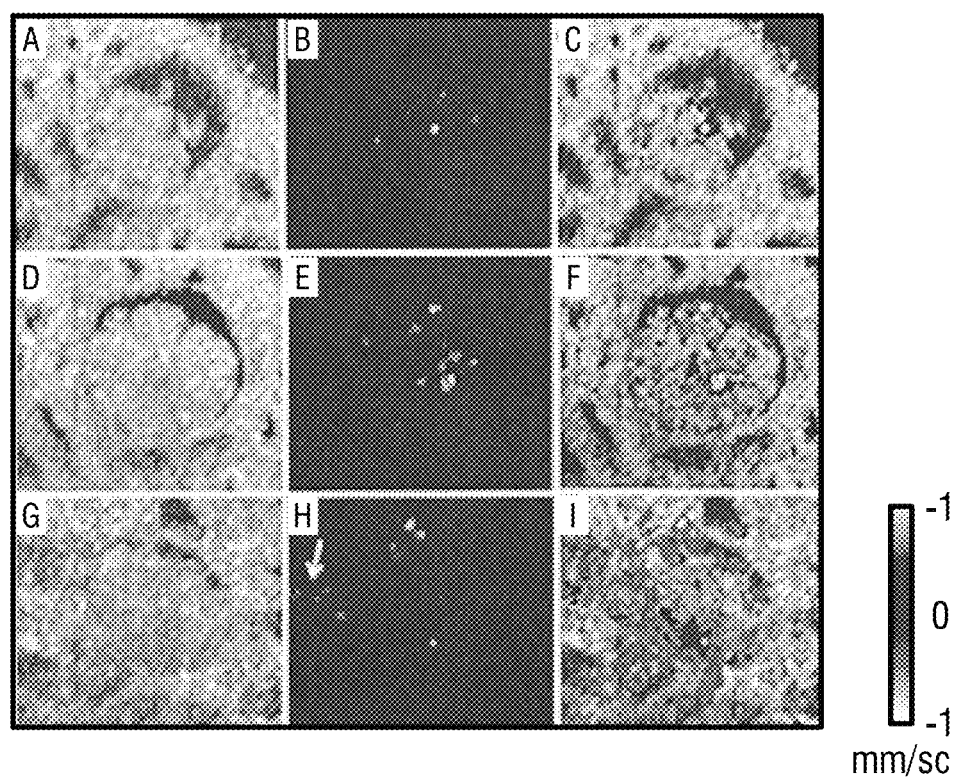
FIG. 2 shows images A-I of optical coherence tomography/Doppler optical coherence tomography (OCT/DOCT) of a rat glomerulus according to the prior art.

Accordingly, FIG. 2, images A, D and G show en face OCT intensity images revealing the kidney microstructure. Uriniferous tubules are readily identified surrounding the glomerulus, which is the circular structure in the middle of the image surrounded by the crescent shaped capsular space of Bowman. FIG. 2, images B, E & H show corresponding DOCT image from the same plane depicting red blood cell (RBC) velocity in numerous glomerular capillaries. As indicated by the color-map (shown in gray scale), red to yellow (bottom of gray scale map) represents increasing velocity of blood flow in one direction while blue to cyan (top of gray scale map) represents increasing velocity of blood flow in the opposite direction. Therefore, the mixture of these colors as represented by the gray scale seen in the DOCT images demonstrates the varying velocities as well as the convoluted nature of blood flow through the glomerular capillaries. FIG. 2, images C, F & I are the fused OCT/DOCT images demonstrating the spatial location of the DOCT signal within the glomerulus.

The effects of acute mannitol and angiotensin II infusion were also observed. DOCT imaging enables real-time monitoring of blood flow changes in three separate physiological states: baseline, following injection of 0.1-0.2 ml mannitol (250 mg/ml), which increases renal blood flow [65-67], and 200 ng/kg body weight angiotensin II [68], which decreases renal blood flow [69-72]. Glomerular blood flow was quantified for the induced physiological states and compared with baseline measurements.

Figure 3:
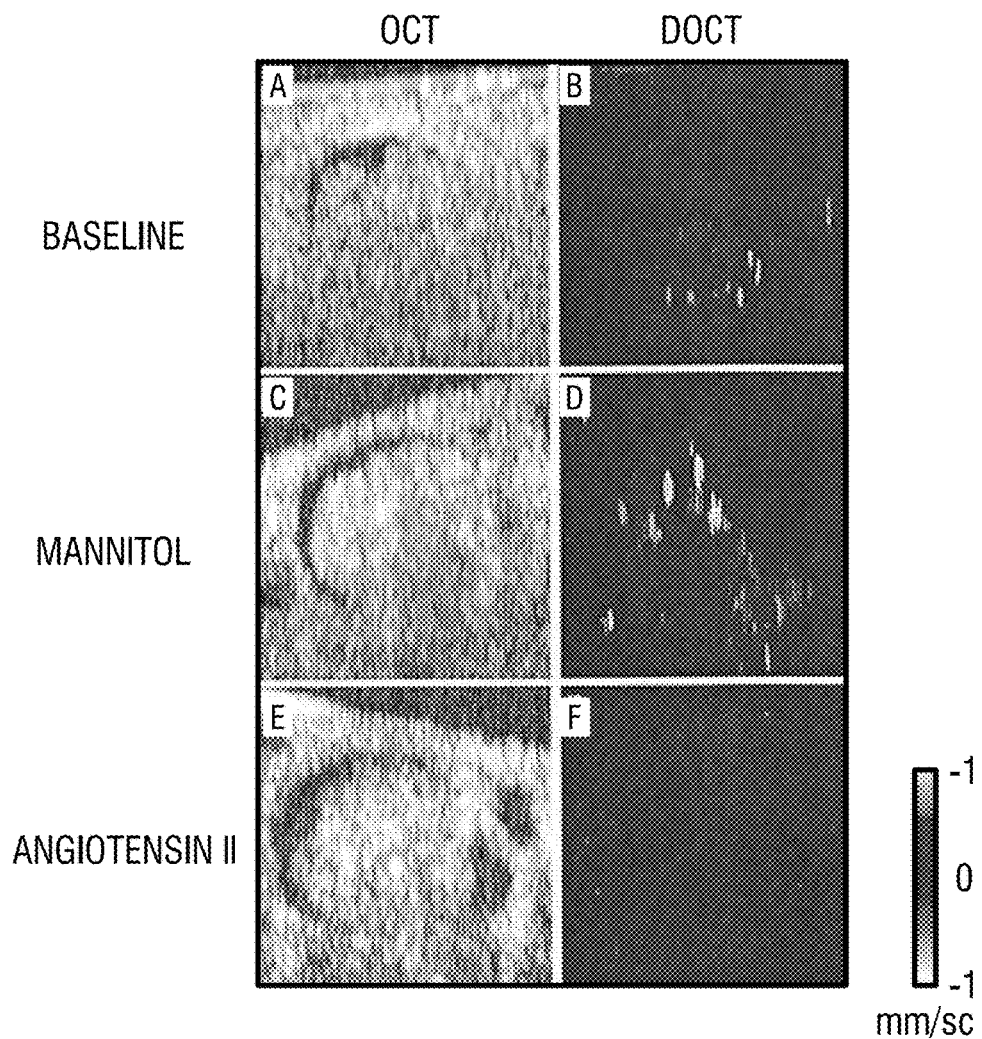
FIG. 3 shows representative OCT and DOCT images (XZ) from 3 different physiological states: images A-B baseline, images C-D after mannitol, and images E-F after angiotensin II according to the prior art.

FIG. 3 (from [32]) shows representative glomeruli imaged under each condition. More particularly, FIG. 3 shows representative OCT and DOCT images (XZ) from 3 different physiological states: images (A-B) baseline, images (C-D) after mannitol, and images (E-F) after angiotensin II. Comparison among the images shows differences in the observed DOCT signal in different glomeruli under altered blood flow conditions. Image size: 294×278 µm. From [32].

Baseline DOCT is depicted in FIG. 3, image B, with mannitol and angiotensin II in image D and image F, respectively. After infusion of mannitol, a significant increase in blood flow was observed, and following infusion of angiotensin II, a significant decrease in blood flow was observed. Corresponding OCT images are presented in images A, C & E for identification of glomerular region in the DOCT images.

Image D DOCT data were subsequently analyzed by computing two parameters: cumulative Doppler volume (CDV) and Doppler flow range (DFR). CDV was calculated by summing together the volume of segmented voxels within the glomerular volume containing DOCT signals that were above the background threshold:

$$CDV = \sum_{xyz} V(x, y, z),$$

where V(x,y,z) is individual voxel volume and the threshold velocity is set to ±0.05 mm/s. Doppler flow was calculated by integrating the DOCT velocity signal over the lateral cross-section (en face) area of the segmented DOCT signal at each depth position. Integration over the en face plane eliminates the angle-dependent uncertainty of the Doppler velocity therefore providing an accurate quantitation of flow as defined by [73]:

$$Flow = \int\int_{xy} v_z(x, y, z) dx dy,$$

where $v_z(x,y,z)$ is the DOCT velocity over the xy segmented DOCT area. DFR was then defined as the flow rate at 99% area under the curve (AUC) of the image D flow histogram.

Figure 4:
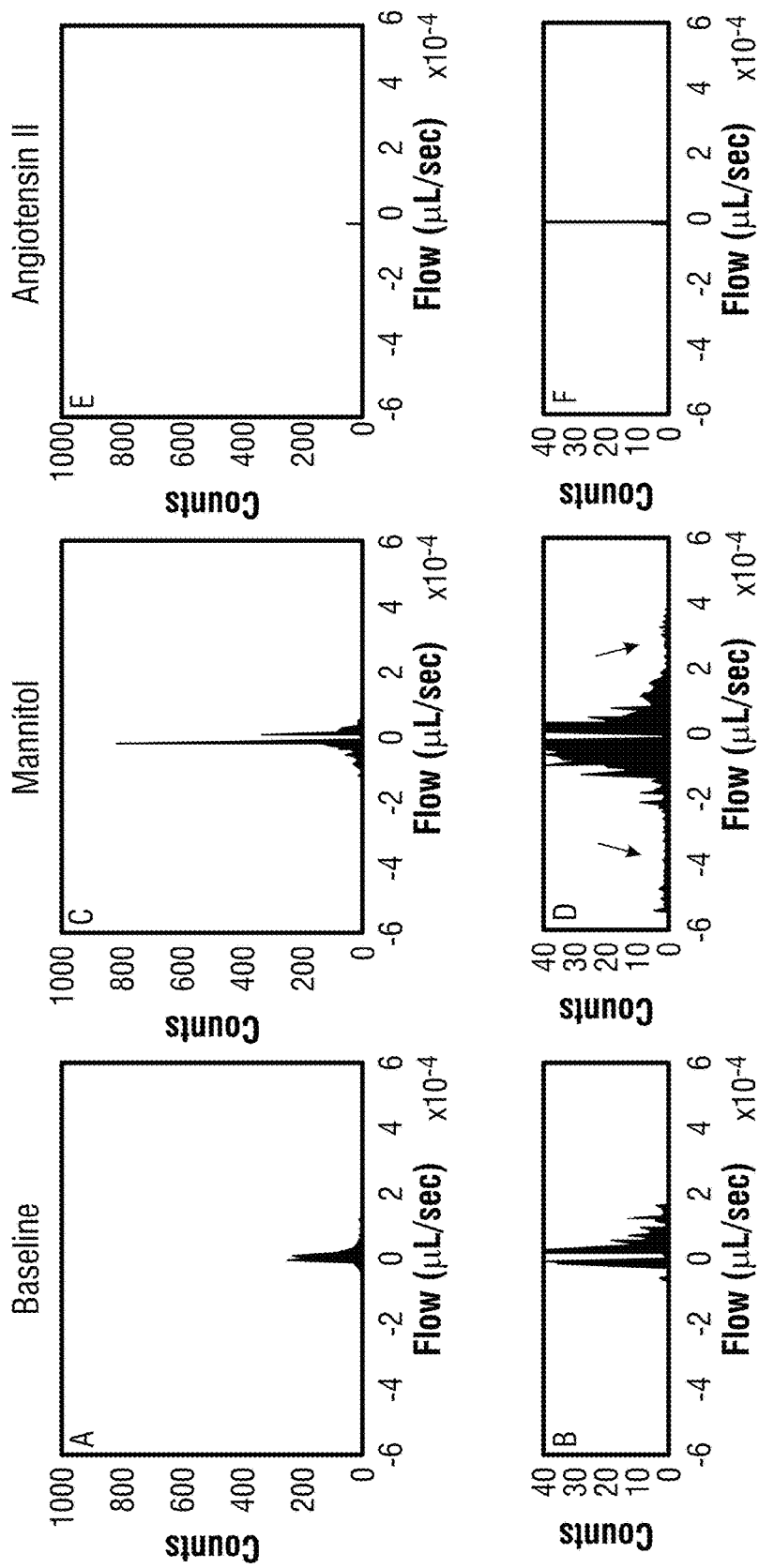
FIG. 4 shows a blood flow histogram comparison according to the prior art wherein images A-B illustrate a baseline blood flow histogram, images C-D illustrate a blood flow histogram following injection of mannitol, and images E-F illustrate a blood flow histogram following injection of angiotensin II.

FIG. 4 shows a blood flow histogram comparison wherein images A-B illustrate a baseline blood flow histogram in number of counts versus flow in microliters/sec (μL/sec), images C-D illustrate a blood flow histogram following injection of mannitol in number of counts versus flow in microliters/sec (μL/sec), and images E-F illustrate a blood flow histogram following injection of angiotensin II in number of counts versus flow in microliters/sec (μL/sec). Each histogram represents a compilation of the segmented DOCT signal at every en face plane through the depth of a single glomerulus. Plots on the lower row are close-up versions at the base of the histograms (below the line) in the upper row. From [32].

Accordingly, FIG. 4 shows the blood flow histograms of three glomeruli to illustrate differences in blood flow rate and blood volume between the induced physiological states. The aforementioned dynamic changes in blood flow detected under altered physiological conditions demonstrate the real-time imaging capability of DOCT to quantitatively image the kidney microvasculature for transplant graft evaluation.

Figure 5:
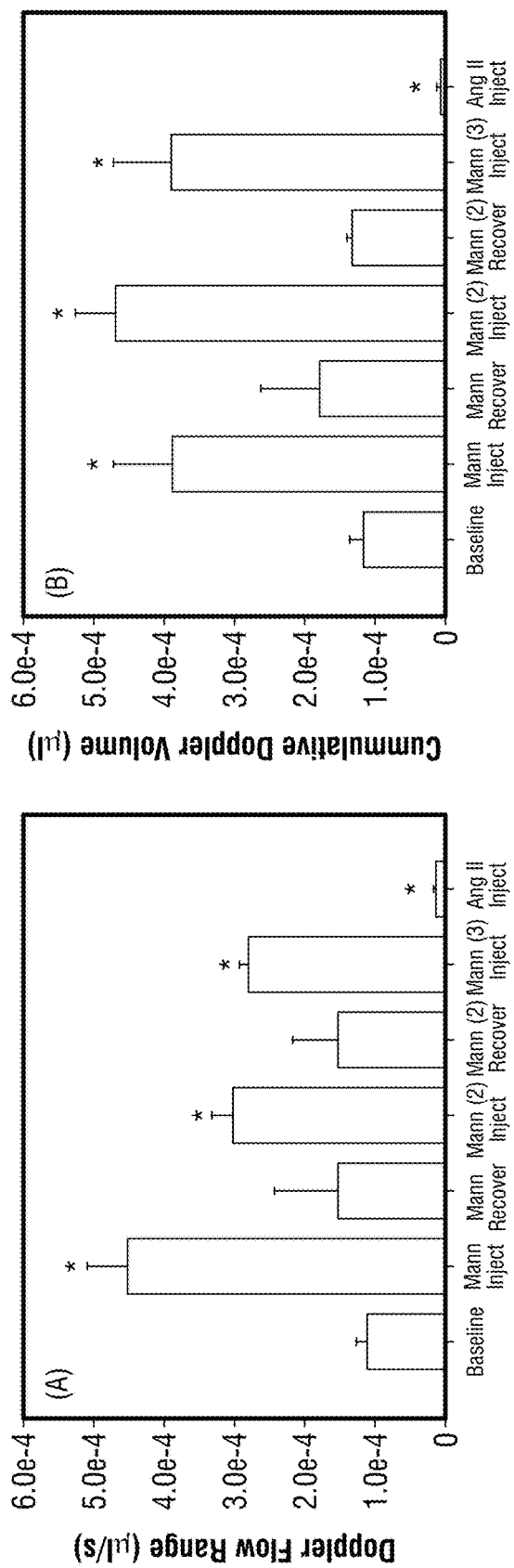
FIG. 5 shows in vivo quantification of DOCT imaging parameters of rat glomeruli according to the prior art wherein image A is a plot of Doppler Flow Range and image B is a plot of Cumulative Doppler Volume.

FIG. 5 shows in vivo quantification of DOCT imaging parameters of rat glomeruli wherein image A is a plot of Doppler Flow Range in μL/s and image B is a plot of Cumulative Doppler Volume in μL. Each of these parameters was measured in multiple glomeruli under 7 separate conditions. Asterisk (*) indicates p<0.05 compared to "baseline." Labels: Mann=mannitol; Ang II=angiotensin II. From [32].

Accordingly, FIG. 5 images A and B show the DFR and CDV values from 7 different physiological states in the same rat. For each state, an average number of n≈4 glomeruli were analyzed. Both DFR and CDV increase dramatically after injection of mannitol. It is interesting to note that after both the first and second mannitol injection, the DFR and CDV values returned to near-baseline levels during the "recovery" period indicating that the effects of the mannitol were wearing off (~15-20 minutes elapsed since injection). Shortly after administering the third mannitol injection to increase blood flow (~10 min), angiotensin II was injected. This injection of angiotensin II reduced both DFR and CDV dramatically, well below the baseline level. This result demonstrates that DOCT can quantitatively image renal blood flow in vivo, thereby providing valuable diagnostic information for vascular function in addition to structural information from OCT. These preliminary results using animal models demonstrate that OCT/DOCT can provide valuable information that would be valuable for determining the status of renal transplants.

C. OCT Imaging of Human Kidney Microstructure

Figure 6:
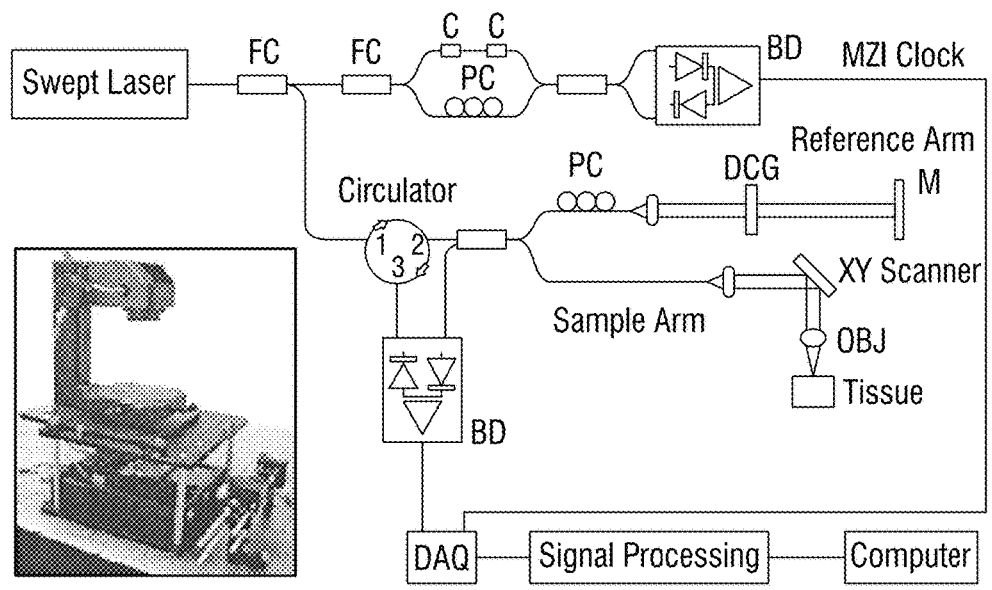
FIG. 6 is a schematic diagram of the Fourier-domain OCT system used in kidney imaging studies according to the prior art wherein the inset at the lower left portion shows a sketch of the OCT microscope of the system.

FIG. 6 is a schematic diagram of the Fourier-domain OCT system used in kidney imaging studies wherein the inset at the lower left portion shows a photo of the OCT microscope of the system. Thus FIG. 6 shows the schematic of the high-speed, high-resolution, Fourier-domain OCT system that was used to obtain the first 3D OCT imaging of human kidneys [74]. A wavelength-swept laser light source generating 100 nm bandwidth at 1310 nm central wavelength was employed, yielding approximately 10-μm axial image resolution in the tissue. The laser used to acquire the preliminary data operates at a sweep rate of 16 kHz and the real-time imaging was performed at 30 frames per second (video rate). A Michelson interferometer composed of a circulator and a fiberoptic 50/50 splitter was used to generate the OCT interference signal. The reference arm consists of a stationary mirror (M) and a polarization controller (PC). The light from the sample arm was steered by a pair of galvanometer mirrors (X and Y), then focused by an objective lens onto the sample. The power on the sample was 4 mW with a spot size of 15 μm. The system's sensitivity was 95 dB.

3D OCT volumes (2.5×2.5×2.5 mm$^3$, with 512×512×512 pixels) were obtained non-invasively from various locations on human kidneys obtained through the Washington Regional Transplant Consortium (WRTC) and preserved (i.e., fixed) with 2% glutaraldehyde.

Figure 7:
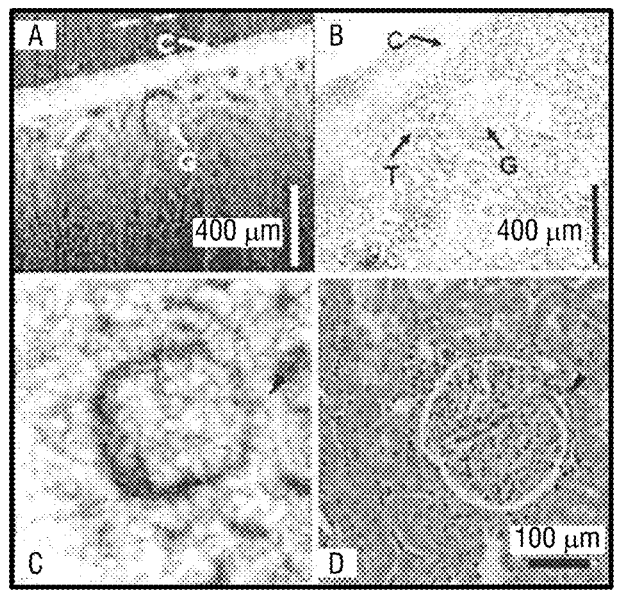
FIG. 7 shows a images A, B, C and D according to the prior art wherein image A illustrates a cross-sectional OCT image of human kidney ex vivo, image B illustrates representative histology of the corresponding area in the human kidney, image C illustrates an en face OCT image of human kidney ex vivo and image D illustrates Histology.

FIG. 7 shows images A, B, C and D wherein image A illustrates a cross-sectional OCT image of human kidney ex vivo. Uriniferous tubules (T), glomeruli (G) and the kidney capsule (C) are distinguishable. Image B illustrates representative histology of the corresponding area in the human kidney (from [74]). Image C illustrates an en face OCT image of human kidney ex vivo. Glomerulus shows light-dense capillary loops surrounded by a ring corresponding to Bowman's space. Image D illustrates Histology (from [75]).

Thus, FIG. 7 (from [75]) shows a representative cross-sectional OCT image of the human kidney and the corresponding conventional light microscopic histology. Because under normal circumstances the kidney will be surrounded by the renal capsule (i.e., thick layer of dense connective tissue), it is important to evaluate OCT's capability to image the tissue structures through the renal capsule. Unlike in the previously described TSCM studies (see above), the presence of the renal capsule did not prevent imaging of sub-scapular kidney tubules and glomeruli. A corresponding histological image (image B) shows correlation of the anatomic features observed by OCT with traditional light microscopic histological sections. Renal glomeruli could also be visualized in the upper cortex as light-dense, round-oval capillary tufts and the Bowman's space as a light-lucent area surrounding the tufts (image C) [75]. These results demonstrated OCT's capability to reveal the histological features in the intact human kidney and underscored its promise for clinical kidney imaging in vivo.

D. Pilot Clinical Trials on OCT Imaging of Renal Transplants

In collaboration with doctors at Georgetown University Medical Center (GUMC), the co-inventors herein performed clinical imaging of human donor kidneys using OCT prior to transplant (i.e., ex vivo) and OCT/DOCT following transplant (i.e., in vivo). The study was approved by the IRB and all patients signed consent forms. The IRB approved the OCT as a "non-significant" risk to the patients.

Figure 8A:
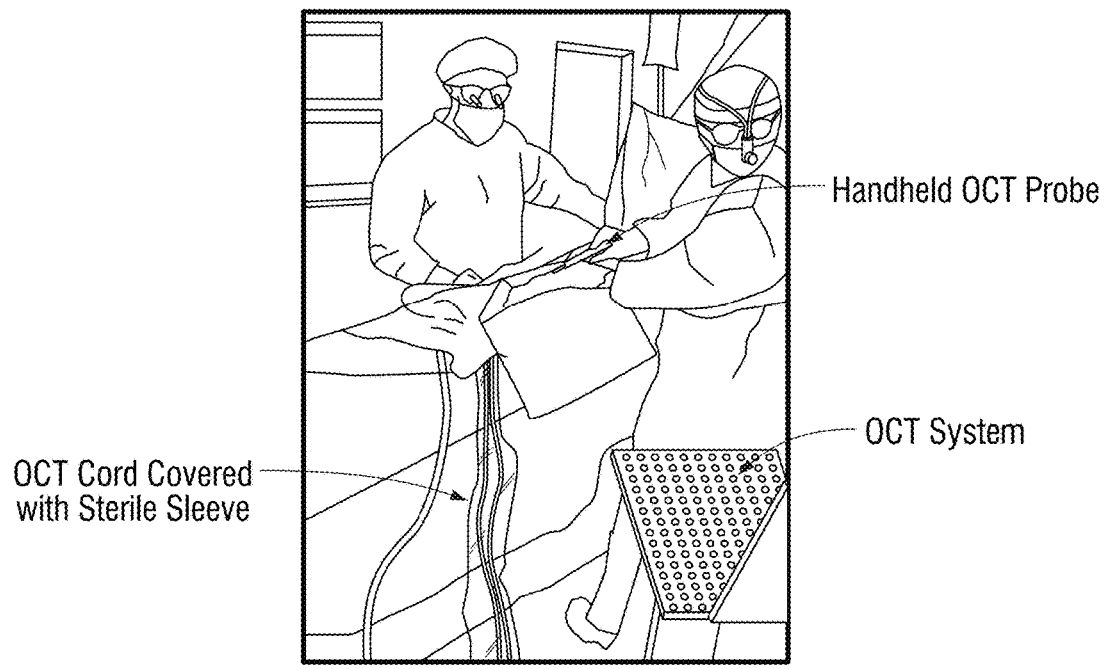
FIG. 8A is a sketch illustrating transplant surgeons using the sterilized hand-held OCT probe of the kidney viability assessment system (KVAS) according to the present disclosure to image a transplanted human donor kidney in the operating room (OR)

FIG. 8A illustrates transplant surgeons using the sterilized hand-held OCT probe of the kidney viability assessment system (KVAS) according to the present disclosure to image a transplanted human donor kidney in the operating room (OR). Both surgeons are looking at real-time images of the functioning kidney while they are imaging it. The OCT probe and associated wires are covered with a sterile camera sleeve.

Accordingly, FIG. 8A shows OCT being used to image a donor kidney following its transplant into a patient. The exemplary portable OCT unit of the KVAS of the present disclosure consists of a portable cart (holding the computer (including at least one processor), laser, optical and electronic components), a handheld probe containing the objective lens, and a real-time user interface or display for image display and quantification. A cage consisting of metallic bars attached to a metallic ring end piece surrounds the imaging objective lens that makes up the hand-held probe. The length of the bars of the cage are adjusted to a proper working distance (i.e., approximately 3 cm) so that any object place near the ring at the end of the cage is within the correct working distance for imaging (i.e., the cage serves as a spacer for correct working distance).

Figure 8B:
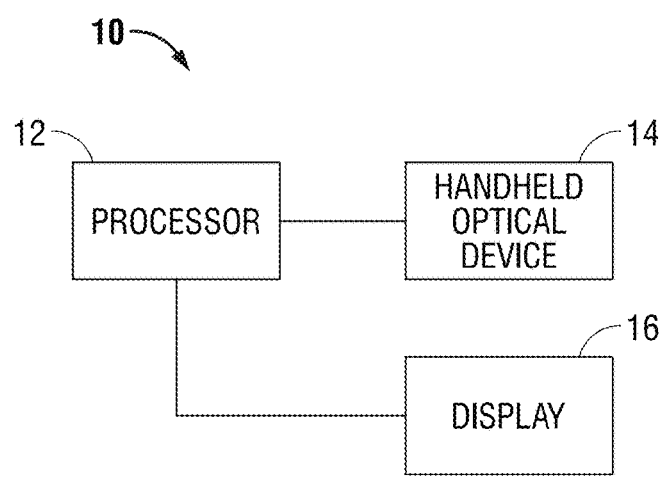
FIG. 8B is a block diagram depicting an exemplary KVAS according to the present disclosure.

FIG. 8B is a block diagram depicting an exemplary KVAS according to the present disclosure. The KVAS designated generally by reference numeral 10 includes at least one processor 12 in operative communication with a handheld optical device 14 and a display 16. The optical device 14 images a donor kidney in vivo and generates at least one image. The at least one image is transmitted to the at least one processor 12. The at least one processor 12 executes a set of instructions corresponding to an algorithm as described herein for processing the at least one image and determining at least one characteristic (e.g., feature, measurement, etc.) corresponding to the viability of the donor kidney.

The at least one processor 12 is also capable of predicting the donor kidney's post-transplant outcome. The system 10 determines at least one characteristic corresponding to the viability of the donor kidney in real-time. According to the present disclosure, the optical device 14 is a handheld optical coherence tomography imaging device and is configured for surveying the entire surface of the donor kidney. The at least one characteristic is indicative of the donor kidney's microstructures and functions. The algorithm segments and quantifies the diameter and/or density of the donor kidney's microstructures and blood flows. The system 10 further includes a display 16 for displaying quantitative values corresponding to the donor kidney determined by the algorithm. The quantitative values can be displayed in real-time.

In designing the KVAS according to the present disclosure to perform their studies, the co-inventors initially encountered two issues: (1) sterility and (2) keeping the laser beam from being impeded by a buildup of moisture on the glass objective lens. Since the hand-held OCT probe was connected to the imaging system by a six foot length of cords, the cords were covered with a sterile sleeve, similar to that used for ultrasound imaging with the sterilized hand-held probe exposed at the end of the sleeve (see FIG. 8A). This set-up worked well for imaging the kidney ex vivo while the donor kidney is being stored in sterile bowl filled with sterile ice (i.e., an ice bath) prior to its transplantation.

However, when the sterilized hand held unit is used to image the donor kidneys following their transplant into the patients, temperature differences between the transplanted kidneys warmed by reperfusion of blood and the colder objective lens within the hand-held probe resulted in a rapid buildup of condensation on the objective lens surface, resulting in a diminished signal. This condensation issue was effectively addressed by covering the entire hand-held probe (containing the objective lens) as well as the six feet of cords with the sterile camera sleeve (see FIG. 8A). A 1 cm circular hole cut in the end of the sleeve permitted unimpeded passage of the laser signal. The circular hole cut in the sterile sleeve was then covered with sterile, adhesive, transparent "Tegaderm" film (available from 3M Health Care, St. Paul, Minn.).

The ultrathin Tegaderm film did not significantly impede the OCT beam, provided a barrier to moisture as well as a sterile interface between the OCT imaging probe and the kidney being imaged. Using this setup, the co-inventors herein imaged the harvested donor kidney with the hand-held OCT imaging probe (covered by a sterile sleeve and Tegaderm) both while the kidney was being stored in the sterile ice bath prior to its transplantation and in situ, following its reimplantation into the recipient. Imaging the entire surface of the harvested donor kidney ex vivo (i.e., both sides and all poles) took less than several minutes and provided a holistic evaluation of the pre-transplant organ.

After transplantation and following revascularization of this same donor kidney within the transplant recipient, OCT/DOCT imaging was performed again to detect Doppler flow as well as morphological features of the transplanted kidney. Once transplanted into the patient, only the upper exposed surface of the kidney was available for imaging. Again, imaging took less than several minutes. This kind of global, non-invasive, real-time histopathological perspective is, of course, not possible when using the invasive, potentially damaging and artifact-prone procedure of excising renal biopsies.

At the Georgetown University Medical Center, kidneys from living donors are protected from ischemia by pretreating the patients with intravenous mannitol (up to 50 g delivered intravenously), flushing the excised kidneys with Viaspan (i.e., also known as the University of Wisconsin solution, i.e., UW solution), and then storage on ice for variable periods of time prior to their transplant. However, Georgetown University Medical Center, as part of the Washington Regional Transplant Consortium/Community, also accepts cadaver kidneys preserved using other procedures including cold storage in Euro-Collins solution and hypothermic pulsatile perfusion preservation.

The co-inventors herein evaluated 35 kidneys from living donors and one that was harvested from a heart-beating cadaver. The co-inventors herein correlated their data with post-transplant renal function, mainly by analyzing post-transplant serum creatinine levels. Serum creatinine levels are the most universal biological marker for estimating the glomerular filtration with a good prognostic value.

Figure 9:
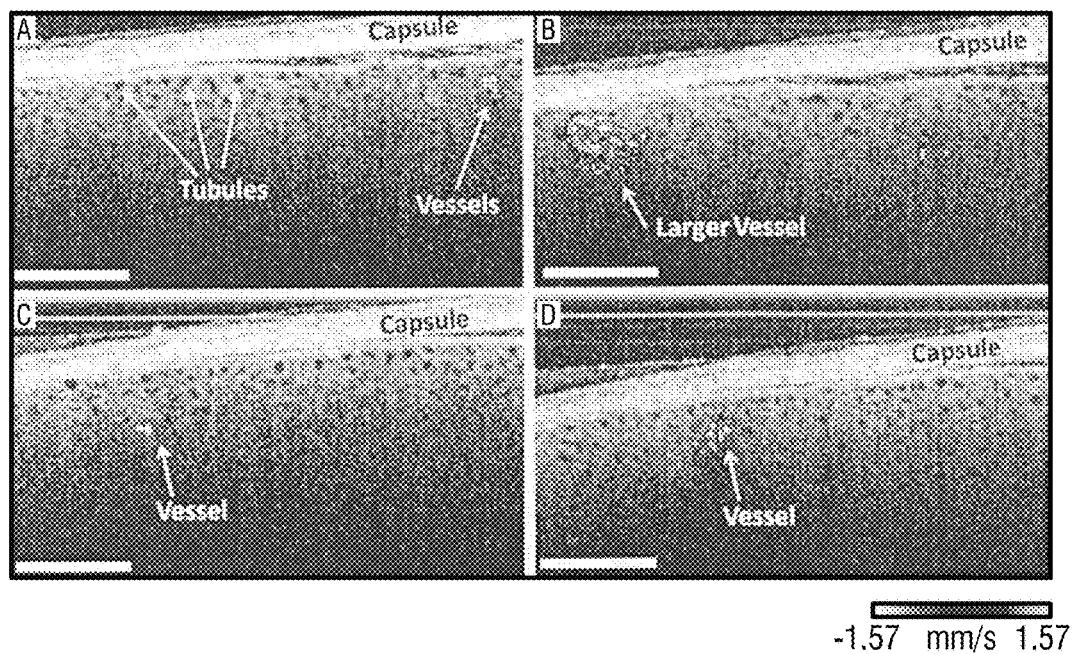
FIG. 9 shows in vivo human kidney images A, B, C and D showing open tubules and cortical blood flow.

FIG. 9 shows in vivo human kidney images A, B, C and D showing open tubules and cortical blood flow. Open tubules appear round and relatively uniform across all images taken by the KVAS according to the present disclosure. Also, a larger blood vessel is seen in image B against some smaller vessels observed in images A, C and D. Scale bar=500 μm, DOCT colormap unit=mm/s.

Thus, FIG. 9 shows representative images of in vivo imaging of subsurface kidney structure and function obtained after transplantation. Renal capsule, parenchyma, and uriniferous tubules are clearly visualized. Three to five layers of tubule lumens are visible and open, denoting active renal filtration and a functioning kidney. Also, blood flow within small and large vessels was captured indicating cortical perfusion within the transplant kidney. These results demonstrate the feasibility of OCT/DOCT imaging of the transplant kidney in the OR room during transplantation procedures. Specifically, the OCT/DOCT following grafting shows both the morphological and functional response of the transplant kidney.

The co-inventors' premise that the openness of the superficial proximal tubules in donor kidneys both prior to and following their transplant can be used to predict post-transplantation renal function was strongly supported by these preliminary clinical trials. Indeed, their preliminary studies have resulted in a modification of how donor kidneys are pretreated prior to being harvested. In the living donors, intravenous infusion of mannitol is infused to protect the kidney tubules from ischemia prior to clamping of the renal vessels and subsequent excision of the donor kidney from the patient (i.e., harvesting the kidney). Mannitol prevents swelling and the resultant damage to the tubule lining cells.

In the co-inventors' studies of living human kidney transplants, the co-inventors found that when the mannitol was infused 30 minutes or more prior to harvesting, the proximal convoluted tubules in donor kidneys prior to their transplant were swollen and the tubule lumens were occluded. However, in three donor kidneys that were harvested within 5 minutes following intravenous infusion of mannitol, the proximal tubules exhibited open lumens when imaged by OCT. These three kidneys with open lumens prior to their transplant, all exhibited dramatically better post-transplant renal function, as indicated by a significantly faster drop in post-transplant serum creatinine levels (i.e., a significantly faster return to normal renal function).

Figure 10A:
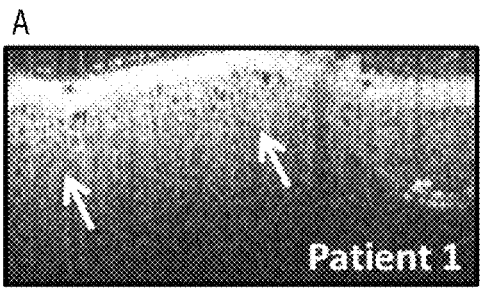
FIG. 10A is a representative OCT image from one human subject of a donor kidney prior to transplantation, Patient 1.
Figure 10B:
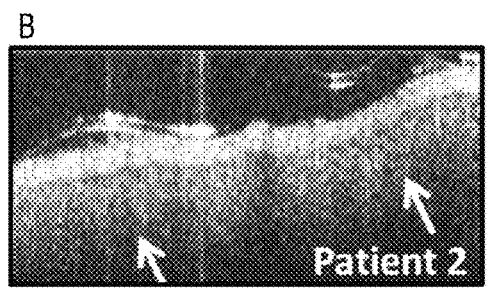
FIG. 10B is a representative OCT image from one human subject of a donor kidney prior to transplantation, Patient 2.
Figure 10C:
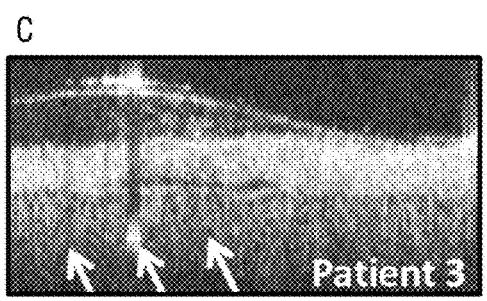
FIG. 10C is a representative OCT image from one human subject of a donor kidney prior to transplantation, Patient 3.
Figure 10D:
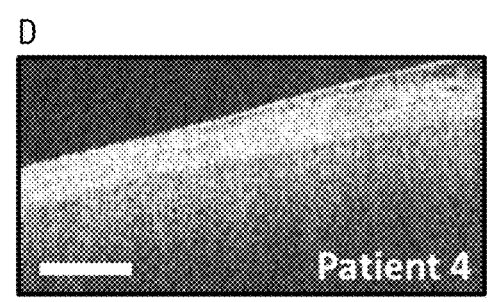
FIG. 10D is a representative OCT image from one human subject of a donor kidney prior to transplantation, Patient 4.
Figure 10E:
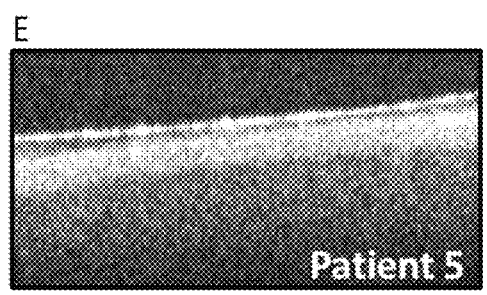
FIG. 10E is a representative OCT image from one human subject of a donor kidney prior to transplantation, Patient 5.
Figure 10F:
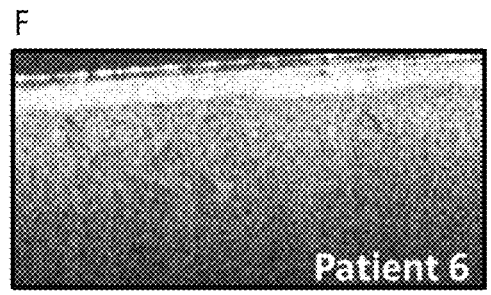
FIG. 10F is a representative OCT image from one human subject of a donor kidney prior to transplantation, Patient 6.
Figure 10G:
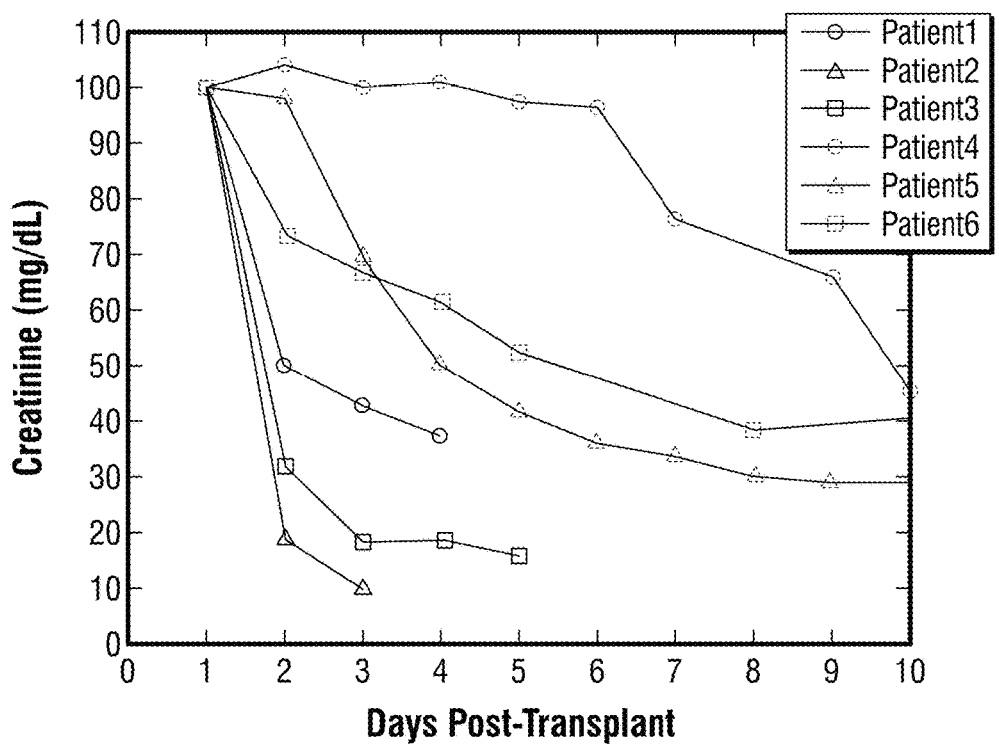
FIG. 10G is a plot of serum creatinine values in mg/dL for Patients 1-6 with OCT imaging data shown in FIGS. 10A-10F from day 0 to day 10 post-transplant.
Figure 10H:
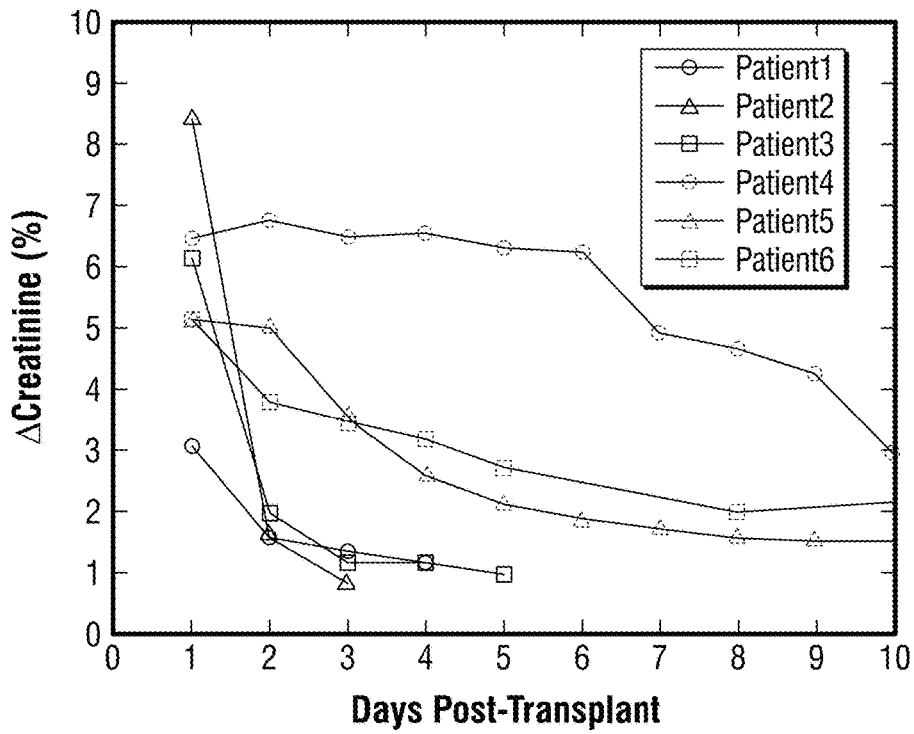
FIG. 10H shows percent change in serum creatinine from day 0 to day 10 post-transplant for Patients 1-6.

FIGS. 10A-10F show OCT imaging of donor kidney prior to transplantation. FIGS. 10A-10F are each a representative OCT image from one human subject, Patients 1, 2, 3, 4, 5 and 6, respectively. FIGS. 10A-10C (Patients 1-3) show opening tubules (see arrows), while in FIGS. 10D-10F (Patients 4-6) most of the tubules are closed. The scale bar=500 µm. FIGS. 10G and 10H illustrate a summary of serum creatinine (SCr) values for 1-10 days post-operative. In FIG. 10G, serum creatinine values in mg/dL are plotted for Patients 1-6 with OCT imaging data shown in FIGS. 10A-10F from day 0 to day 10 post-transplant. Patients 1-3 (corresponding to OCT FIGS. 10A-10C) shows fast drop in Scr, while Patients 4-6 (corresponding to OCT FIGS. 10D-10F) takes longer time for SCr values to return. FIG. 10H shows percent change in serum creatinine from day 0 to day 10 post-transplant for Patients 1-6.

Specifically, in all three cases the serum creatinine levels returned to within normal values (i.e., less than 1.5 mg/dL) within two days, while the patients with living donor kidneys that did not reveal open tubules prior to transplantation had post-transplant serum creatinine levels that remained elevated for seven days or longer prior to returning to within normal values (see FIG. 10G). These observations support the co-inventors' earlier DOCT studies of rat kidneys wherein the effects of the mannitol injection were wearing off ~15-20 minutes following injection. While mannitol is believed to have a half-life of 1-2 hours, the foregoing observations indicate a need to harvest living donor kidneys within minutes following mannitol infusion.

In addition, imaging the kidney following its transplant also proved useful in revealing of post-transplant renal function. While 14 of the living donor kidneys eventually returned to normal renal function within 3 weeks following their transplant (as indicated by serum creatinine values), in one case the serum creatinine remained elevated has not yet (i.e., 3 months later) returned to normal. This kidney had suffered additional normothermic ischemia due to revascularization problems encountered during the implantation procedure. This also, was the only donor kidney that revealed no open renal tubules when examined using OCT following its implantation into the recipient. The elevated serum creatinine levels resulted in a biopsy to determine if the elevated serum creatinine levels represented rejection. Histopathological analysis verified that the elevated serum creatinine levels were a result of ischemia rather than rejection. The foregoing preliminary observations both strongly support our premise that the openness of the uriniferous tubules is a direct reflection of post-transplant renal function.

III. Objectives/Specific Aims/Hypothesis

The co-inventors herein were limited to living donors because the OCT unit is not on site at Georgetown Medical Center. Rather, Dr. Yu Chen also uses it in ongoing experiments. Therefore, the co-inventors herein need time to disassemble the OCT unit, transport it to Georgetown, and reassemble it prior to clinical imaging. The time element limited the co-inventors to living donors, wherein the transplants are scheduled in advance. Cadaver kidneys, on the other hand, require an onsite unit because of the short time period between being notified of donor kidney availability and its subsequent transplant. While the co-inventors' data with living donors has proven extremely useful (see preliminary results above), the co-inventors herein expect the OCT to provide even more valuable information about cadaver kidneys. Specifically, previous animal studies have shown a good correlation between tubule morphology and post-transplant function.

In the present disclosure, the co-inventors placed state-of-the-art OCT units on site at the transplant centers. Therefore, the co-inventors herein were able to image cadaver kidneys and determine whether or not these kidneys are in good enough condition to transplant regardless of other known and unknown factors (e.g., storage time, means of preservation, donor age, health, etc.). Of course, developing algorithms, as proposed in the present disclosure, will facilitate the ability of even untrained personnel to make these important decisions with a minimal amount of training. The final result will enable transplants units to make optimal use of the available donor kidney pool, thereby increasing the number of available kidneys, preventing the use of kidneys that would not function properly following transplant, and facilitating post-transplant adjunct therapy by predicting the extent of post-transplant acute tubular necrosis.

Objectives:

The co-inventors undertook clinical trials involving OCT and DOCT imaging donor kidneys prior to and following renal transplant. These OCT and DOCT imaging studies were correlated with post-transplant renal function in order to establish imaging guidelines (and associated algorithms) for DOCT/OCT imaging of kidneys prior to and following their transplant.

Hypothesis:

The co-inventors central hypothesis was that the morphological and functional parameters as measured by OCT/DOCT using the KVAS of the present disclosure can be used to accurately determine post-transplantation renal function.

Specific Aims:

Aim 1. Image human kidneys in three-dimension using a handheld high-speed OCT imaging device of KVAS prior to and following kidney transplantation procedures.

Aim 2. Develop three-dimensional image processing algorithms to quantitatively assess the morphometric parameters (e.g., tubular lumen diameters) and functional parameters (microvascular blood flow) as indicators of the functional status of kidneys.

Aim 3. Derive the diagnostic criteria for assessing transplant kidney function and perform prospective clinical studies to assess the accuracy of predicting post-transplant function using the OCT.

C. Research Strategy

Aim 1. Image human kidneys in three-dimension using a handheld high-speed OCT imaging device of KVAS prior to and following kidney transplantation procedures.

Study Design:

This part of the study involved imaging donor kidneys prior to their transplantation and immediately following their implant into the patient. The kidneys that were imaged came from both living and non-living donors. At the Georgetown University Medical Center, the procedure for preserving kidneys is flushing with Viaspan (i.e., also known as the University of Wisconsin solution, i.e., UW solution) and storage on ice for variable periods of time (not to exceed 36 hours) prior to their transplant. However, Georgetown University Medical Center, as part of the Washington Regional Transplant Consortium/Community, also accepts kidneys preserved using other procedures including cold storage in Euro-Collins solution and hypothermic pulsatile perfusion preservation. Hence, kidneys that have been stored using a variety of the most commonly used storage procedures were evaluated over time.

After informed consent, imaging is then performed on patients clinically indicated to undergo kidney transplantation as the standard of care. Taking into consideration that some of the over 60 patients receiving transplants per year at the Georgetown University Medical Center may not sign the consent forms, it is conservatively estimated that approximately 50 kidneys will be imaged during each year of the study. Therefore, a total of 200 kidneys will be imaged during the course of the proposed studies beginning in 2015 (i.e., 4 years×50/year=200) at the Georgetown University Medical Center. In the study (which began in 2014) patients undergo standard protocol in preparation for surgery. During standard transplantation procedure, the handheld OCT imaging probe (covered by a sterile sleeve) is placed on the transplant kidney. OCT imaging is performed on both sides of the donor kidney prior to transplant (~20 regions) in order to provide an overall (i.e., global) assessment. OCT imaging is performed before and after transplantation of the kidney. Post-transplant patient data that is collected includes demographic data and details of medical history including age, gender, etiology of chronic kidney disease, the presence or absence of diabetes, hypertension, and other comorbidities. Laboratory data extracted from the patients' charts and from the electronic laboratory database of the hospital include the following: serum creatinine, blood urea nitrogen (BUN), estimated glomerular filtration rate (eGFR), serum albumin, serum hemoglobin (Hb), transferrin saturation (TSAT), and C-reactive protein, immunosuppressive treatment. These measurements are then correlated with optical imaging parameters (see Aims 2 & 3).

Methods:

3D imaging is helpful to kidney imaging as it provides not only comprehensive volumetric information, but also enables integration of DOCT signals over en face plane to quantify flow information correctly [73]. 3D imaging in vivo requires high-speed laser source. In the study described herein, the co-inventors use the new commercially available 55 kHz swept-source OCT (SS-OCT) imaging system from Thorlabs Inc., which employs a novel tunable filter technology with a highly efficient laser cavity design to achieve a broad wavelength tuning range (>120 nm) at high sweep rates. Excellent coherence length (6 mm) is maintained during the high-speed tuning of the swept source laser, which supports greater OCT imaging depths and higher imaging rates in samples compared to our currently available 16 kHz SS-OCT imaging system. 3D OCT volumes with 256×256×512 pixels can be acquired in ~1 second, thereby reducing the motion artifacts significantly.

In addition, Thorlabs developed a VCSEL-based swept source laser running at 100 kHz axial scan rate at 1.3 µm with 100 nm tuning range [76]. This novel light source is a new clinical tool capable of in vivo, volumetric imaging of tissue pathology with an unprecedented axial scan rate. The co-inventors herein adapted this novel OCT light source for applications in kidney transplant imaging.

In addition, the co-inventors herein developed phantoms to quantitatively extract essential parameters that govern image quality, namely, image resolution (how clear the co-inventors herein can image) and image sensitivity (how deep the co-inventors herein can see). Those phantoms resulted from Dr. Chen's collaboration with FDA, for example, a nanoparticle-based phantom to calibrate OCT resolutions in 3D [77]. In this study, the co-inventors herein also developed a scattering phantom with similar optical properties as human kidney. The OCT systems are calibrated each time before patient imaging, and the calibration data is saved for record.

Potential Limitations and Alternatives:

Motion artifacts might be present during imaging acquisition. The co-inventors herein can stabilize the kidney against the abdominal wall using standard instruments to reduce motion artifacts while imaging. The OCT hand-held probe is also gently placed on the kidney surface to further minimize motion. If needed, the OCT probe can be placed on an articulating arm to reduce the tremor of the surgeons' hand. Furthermore, the co-inventors herein applied cross-correlation algorithms to correct the motion artifacts [78].

Aim 2. Develop 3D image processing algorithms for the KVAS to quantitatively assess the morphometric parameters (e.g., tubular lumen diameters) and functional parameters (microvascular blood flow) as indicators of the functional status of kidneys.

Study Design:

Our animal and human studies undertaken thus far have indicated that there are a number of likely morphological parameters that are candidates for algorithm-based image processing to determine post-transplant renal function. One is the mean tubule lumen diameter. Our studies have shown that more open the tubules reflect better post-transplant function. Second is the variability in average tubule luminal diameter. The latter may reflect the fact that S1 segments of the proximal convoluted tubules appear to be more sensitive to ischemia than S2 segments as was seen by us in a previous study of ischemic rodent kidneys [79]. However, S2 proximal tubule segments make up the majority of cortical proximal convoluted tubules and the relative role of ATN associated with S1 versus S2 in human kidneys is not yet known.

Third is the irregularity in the profiles of the tubule lumens. Irregular profiles in the tubule lumens can result from cellular debris (mainly from a disrupted microvillous brush border) lining the tubule lumens and from cell swelling. Fourth is the number of open tubules per unit area of cortex (tubular density), and fifth the total tubule luminal space per unit area of cortex. The latter parameter may be the most important because it reflects the overall available filtering surface area in the donor kidney.

Together, these foregoing parameters reflect the tubule cell damage resulting from acute tubular necrosis (ATN), which is the main insult resulting in post-transplant renal failure in transplanted donor kidneys. As previously noted, the co-inventors herein found that these kind of parameters can predict the extent of ATN in a renal transplant animal model [7]. It should be noted, however, that the data collected in this earlier study were derived from the most superficial proximal convoluted tubules (i.e., one layer deep in the kidney cortex) using TSCM.

Using OCT, the co-inventors herein are able to see four to five layers deep in the human kidney even with an intact renal capsule. The newer OCT units used in the studies provide for even deeper penetration into the kidney parenchyma. Therefore, the co-inventors herein are able to image significantly more proximal convoluted tubules than those can be imaged using the aforementioned TSCM imaging. Nevertheless, as previously mentioned, it is important to note that the status of superficial proximal tubule reflects the status of proximal tubules throughout the renal cortex (i.e., those deeper in the cortex).

The degree of ATN suffered by individual kidneys depends also on a variety of factors including preservation methods and donor background (i.e., age, health, race, etc). Co-inventors herein have previously reported that even the amount of protein in the diet can significantly affect post-ischemic ATN [80]. Therefore, it is very difficult to predict the degree of ATN suffered by a kidney prior to its transplant without some objective measure. By using OCT, the transplant surgeon can make the most efficient use of available donor kidneys (including the use of kidney from non-heart beating cadavers), eliminate the possible use of bad donor kidneys, provide a measure of expected post-transplant renal function, and allow better distinction between post-transplant immunological rejection and ischemic-induced acute renal failure. These conclusions are strongly supported by co-inventors' clinical trials, which indicated that when OCT imaging revealed open proximal tubules in living donor kidneys prior to their transplant, these kidneys would exhibit significantly improved post-transplant renal function. Also, that when open tubules are not seen in the post-transplanted donor kidney, the kidney can be expected to exhibit poor post-transplant renal function due to ATN (not rejection).

Immediately following transplant of the donor kidney into the recipient, the co-inventors herein again measured the forgoing morphological parameters followed by an assessment of renal microvascular blood flow using DOCT. Using an animal model, the co-inventors herein were able to image microvascular flow by DOCT within individual glomeruli, thereby providing an estimation of glomerular filtration rate (GFR). Unlike the kidney proximal convoluted tubules, that respond uniformly to renal insults, however, glomeruli may vary considerably in their functional status. However, with OCT, the co-inventors herein were able to image several layers deep into the kidney parenchyma even through an intact kidney capsule. It is therefore possible that by surveying the entire kidney surface enough superficial glomeruli is revealed in order to obtain significant information from donor kidneys. The data obtained from the OCT prior to transplant and the OCT/DOCT data following transplant is correlated with post-transplant functional parameters (noted above). This information was then be used to create quantitative algorithms (see Aim 3) in order to facilitate the evaluation of donor kidneys by OCT/DOCT in the clinical setting.

Methods:

To provide diagnostic information obtained by 3D-OCT, there is a need to develop automatic image-processing methods in accordance with the present disclosure to quantitatively evaluate kidney morphology. Computer-aided analysis promises to automatically analyze a large volume of data quickly, and therefore will be very helpful for providing the clinicians with quantitative diagnostic information in a timely manner and minimizing the inter- and intra-observer errors.

With this in mind, the co-inventors herein developed an automatic image-processing algorithm to be implemented with and be part of KVAS in accordance with the present disclosure to quantitatively evaluate the imaging parameters of kidney microstructures, such as tubular diameters and density.

Figure 11:
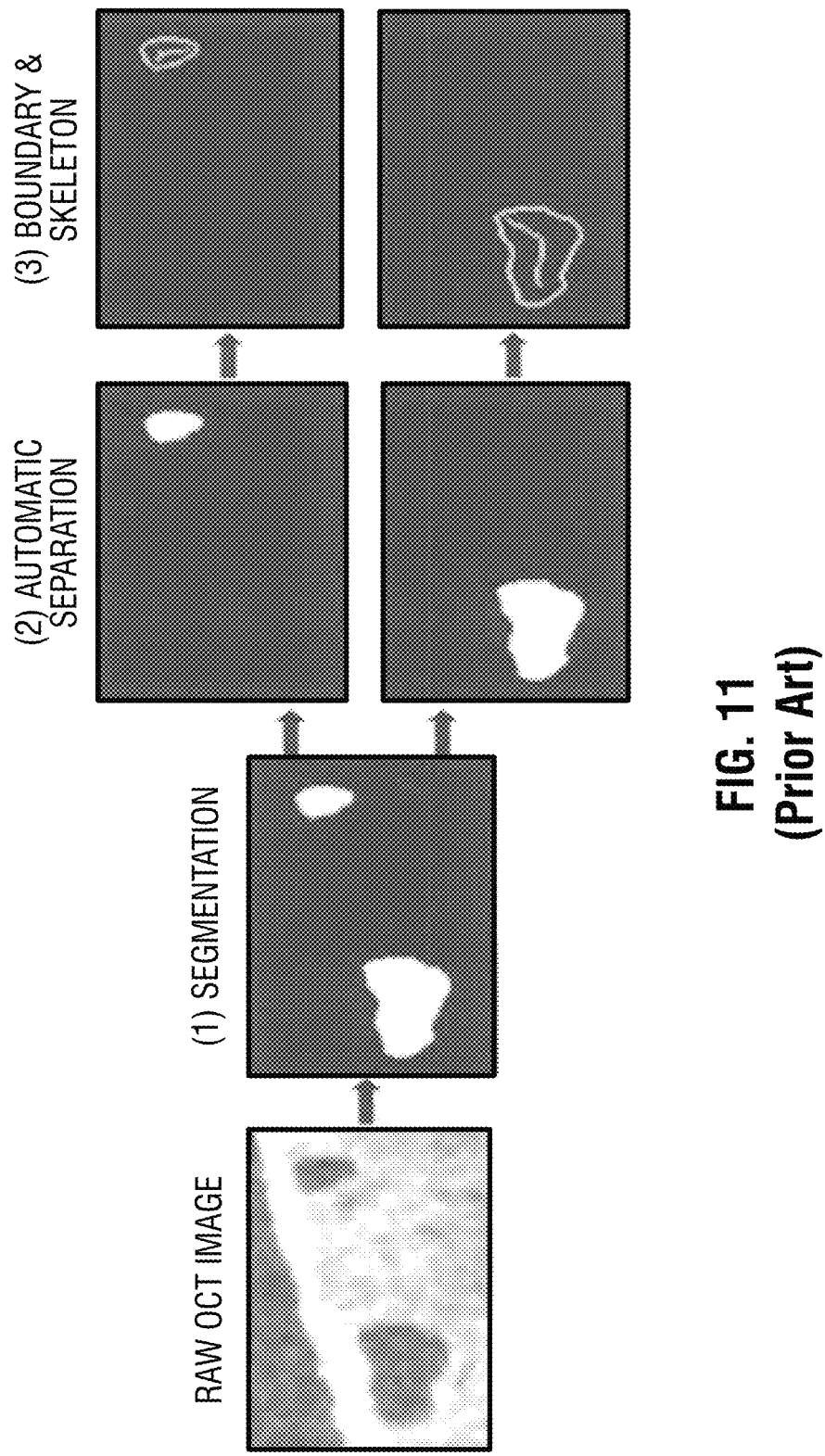
FIG. 11 shows a flow chart of an automatic image processing algorithm according to the prior art which includes four major steps: 1) image segmentation from the raw OCT image; 2) automatic region separation and selection; 3) finding the boundary and skeleton for each isolated regions to calculate the mean tubular diameter, and 4) sum all segmented regions to estimate the tubular volume.

FIG. 11 shows a flow chart of an automatic image processing algorithm according to the prior art which includes four major steps: 1) image segmentation from the raw OCT image; 2) automatic region separation and selection; 3) finding the boundary and skeleton for each isolated regions to calculate the mean tubular diameter, and 4) sum all segmented regions to estimate the tubular volume. Computer estimated results have been validated with manual measurements. From [74].

More particularly, the algorithm for tubular diameter quantification includes three major steps: 1) Automatically segment the kidney structures (such as tubules) from the kidney parenchyma using their distinct backscattering intensities; 2) Automatically separate each isolated (not connected) tubular segment by an intelligent image-processing algorithm, which automatically fills each region to its boundary and assigns an index value to every segmented region of interest (ROI).

The novel approach according to the present disclosure allows different regions to be individually selected for further analysis; 3) Quantify the average diameter of each region as follows: the boundary (B) and skeleton (S) of each segmented region are automatically generated using morphological thinning, and the local radius for every pixel (b) on the boundary (B) is calculated by using the shortest distance between the pixel (b) to the skeleton (S), i.e., $$\text{Radius}(b) = \min_{\forall s \in S}\left(\mathit{dist} \cdot (b, s)\right).$$

The averaged dimension of each region is then calculated by averaging all boundary pixels. In addition, tubular density can be quantified by dividing the sum of the segmented tubular regions by the total renal region (tubules plus parenchyma). Furthermore, DOCT parameters (DFR and CDV) can be quantified using the algorithm described previously.

Figure 12:
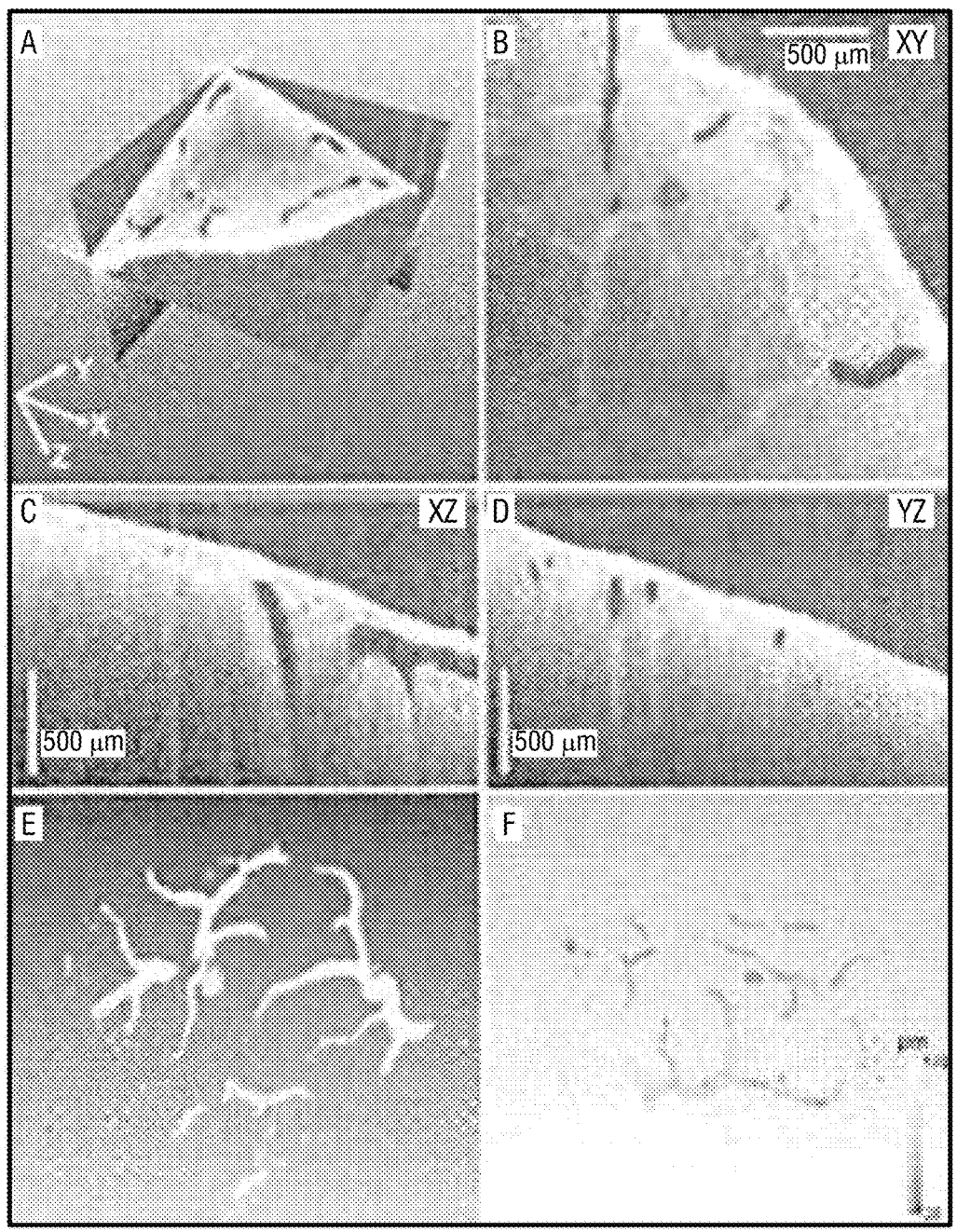
FIG. 12 illustrates images of the human kidney according to the prior art wherein image A illustrates a 3D cut-through view of the human kidney (case 1, images B-D are representative OCT images, image E is a 3D volumetric image of the segmented renal vasculature and image F illustrates automatic quantification of the vessel diameter and color-coded in gray scale on the structural image.

FIG. 12 illustrates images of the human kidney wherein image A illustrates a 3D cut-through view of the human kidney (case 1). The renal blood vessels as well as the kidney parenchyma are visualized. Images B-D are representative OCT images. Image E is a 3D volumetric image of the segmented renal vasculature. Image F illustrates automatic quantification of the vessel diameter and color-coded in gray scale on the structural image (images A-F from [74]).

More particularly, in FIG. 12, image A is the 3D view of one representative ROI (Region of Interest) in a human kidney ex vivo (case 1). Images B-D show the representative images along the three orthogonal planes (XY, YZ, XZ). Detailed kidney vascular structures can be visualized in all these image planes. Image E shows the segmented 3D vascular tree. Image F shows the automatic quantification of vascular diameters for different regions, which ranges from 30-150 μm.

Figure 13:
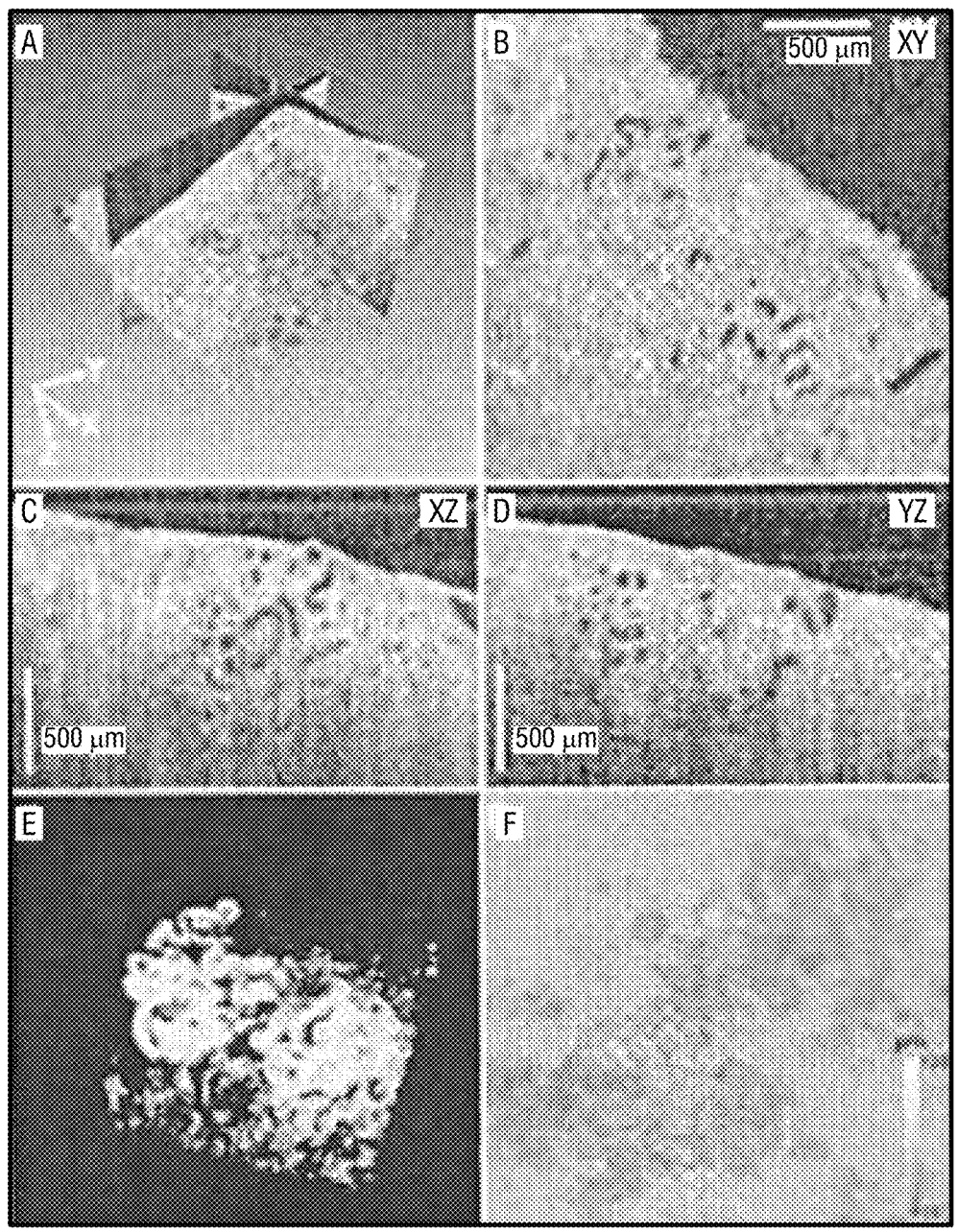
FIG. 13 illustrates images of the human kidney according to the prior art wherein image A illustrates a 3D cut-through view of the human kidney (case 2), images B-Dare representative OCT images, image E is a 3D image of the segmented distended convoluted tubules and image F illustrates automatic quantification of the tubular diameter.

FIG. 13 illustrates images of the human kidney wherein image A illustrates a 3D cut-through view of the human kidney (case 2). The distended convoluted tubules as well as the kidney parenchyma are visualized. Images B-D are representative OCT images. Image E is a 3D image of the segmented distended convoluted tubules and image F illustrates automatic quantification of the tubular diameter. From [74].

More particularly, in FIG. 13, image A is the 3D view of another ROI from a different human kidney ex vivo (case 2). Images B-D show the representative images. Detailed kidney tubular structures can be visualized in all these image planes. OCT shows distended convoluted tubular structure, which is clearly visualized in the segmented 3D view, as shown in image E, where comprehensive examination of morphological features, such as the tubular curvature and interconnectivity, is possible. Image F shows the automatic quantification of tubular diameters for different regions. The distended tubular lumen shows approximately 70-90 µm in diameter.

Figure 14:
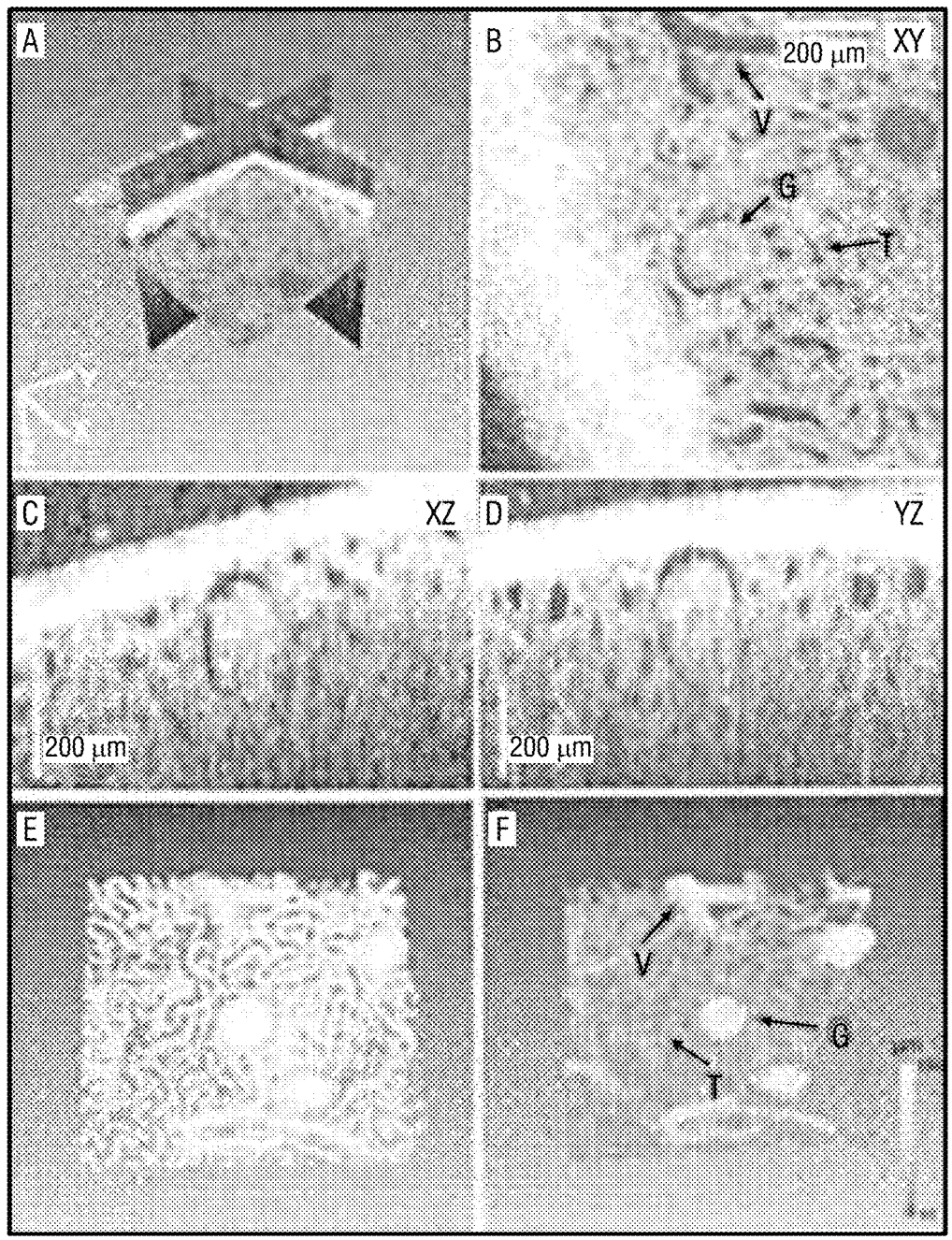
FIG. 14 illustrates images of the human kidney according to the prior art wherein image A illustrates a 3D cut-through view of the human kidney (case 3), images B-D are representative OCT images, image E is a 3D view of the segmented renal microstructures and image F illustrates automatic quantification of the lumen diameter.

FIG. 14 illustrates images of the human kidney wherein image A illustrates a 3D cut-through view of the human kidney (case 3). Various renal microstructures including the blood vessels (V), uriniferous tubules (T), and glomeruli (G) are visualized. Images B-D are representative OCT images, image E is a 3D view of the segmented renal microstructures and image F illustrates automatic quantification of the lumen diameter. From [74].

In FIG. 14, image A is the 3D view of the third example of human kidney ex vivo (case 3). Images B-D show the representative images. Detailed kidney microstructures can be visualized in all these image planes. Image E shows the segmented 3D structures. Image F shows the automatic quantification of lumen diameters for different regions. The glomeruli are surrounded by an expanded network of uriniferous tubules and blood vessels. The diameters of the glomeruli are measured to be approximately 200 µm. These results show the capability of OCT to visualize and quantify renal microstructures. The quantification accuracy of this procedure has been validated by conventional histological analysis.

Additional 3D automated algorithms for KVAS need to be developed in order to further develop for: 1) classifying different renal structures such as tubules, glomeruli, and vessels; and 2) determining tubular diameters and densities in 3D. Our preliminary image classification algorithm operates on the isolated ROIs of each 3D set of kidney images obtained from OCT segmentation.

Figure 15A:
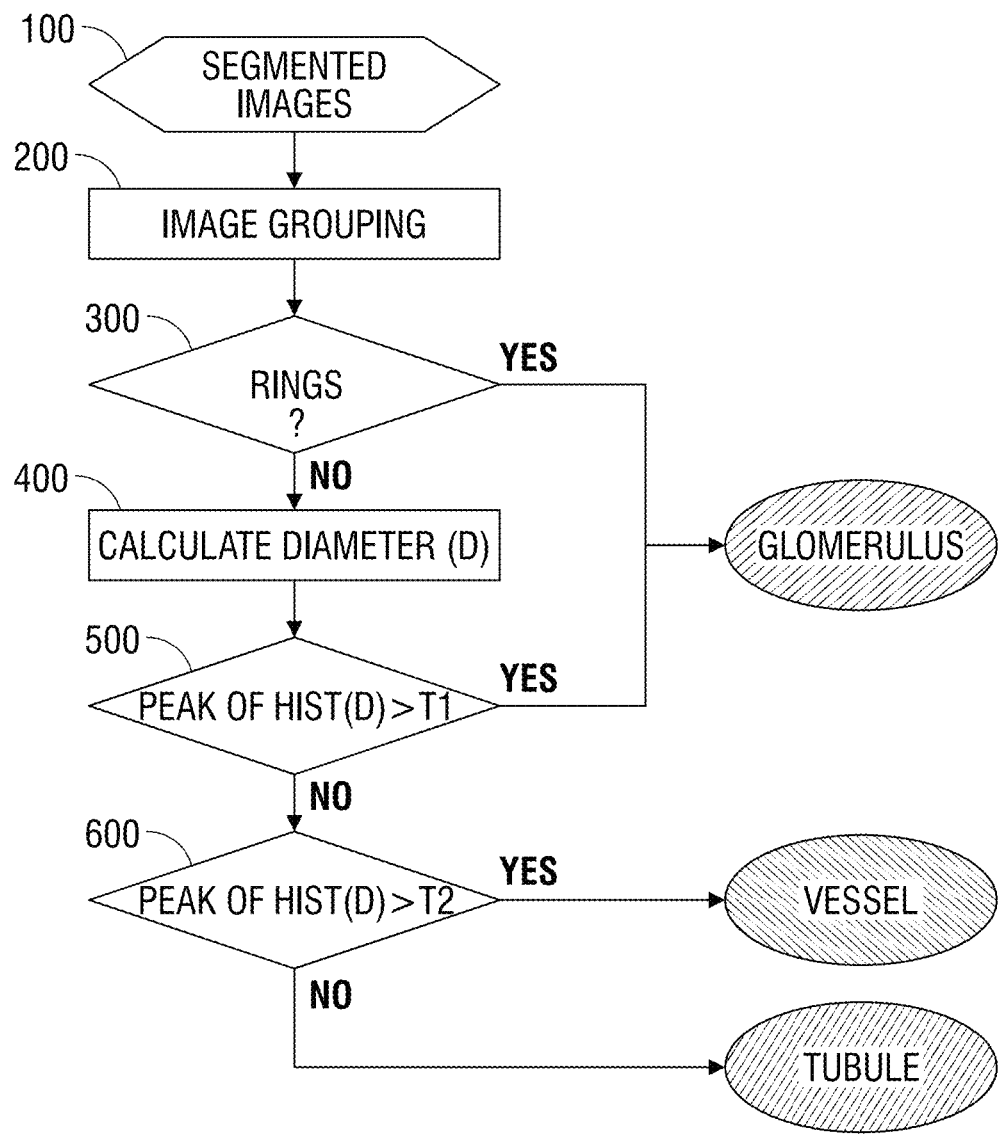
FIG. 15A shows a flow chart of the human kidney image classification algorithm of the KVAS according to the present disclosure.

FIG. 15A shows a flow chart of the human kidney image classification algorithm of the KVAS according to the present disclosure. Hist (D) means the histogram of diameter; T1 and T2 are empirical thresholds.

Figure 15B:
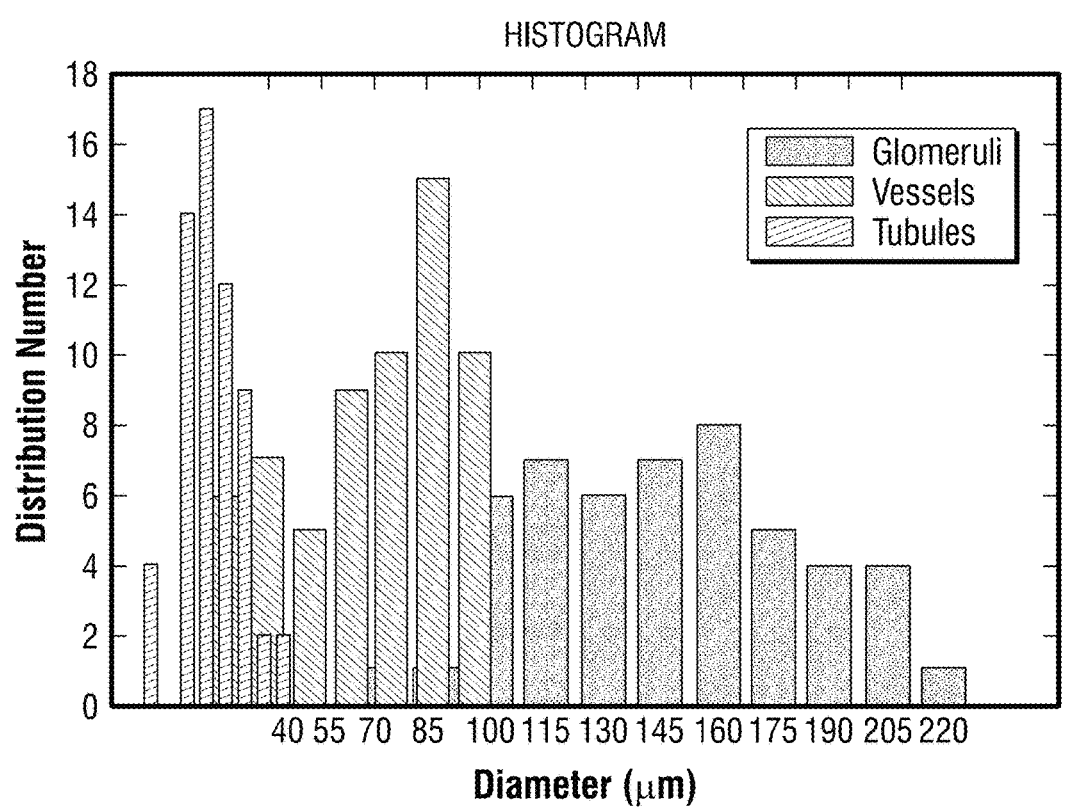
FIG. 15B illustrates an exemplary histogram depicting the size distribution of kidney structures (glomeruli, blood vessels, and tubules)

Accordingly, a flowchart describing the classification algorithm of KVAS according to the present disclosure is shown in FIG. 15A. Classification of kidney structures is based on each set of spatially interconnected image voxels (groups). The co-inventors herein developed a 3D labeling algorithm to automatically identify regions that are spatially connected in 3D [81]. After labeling, label indices can be used to select and extract stereo-isolated groups from the kidney. Each region is a group representing interconnected renal structures. FIG. 15B is an exemplary histogram depicting the size distribution of the classified kidney structures (i.e., glomeruli, blood vessels, and tubules).

In the image classification according to the present disclosure, the object is the isolated ROIs (regions of interest) of a set of kidney images obtained by OCT (block 100 in FIG. 15A). FIG. 15A depicts the general structure of the flow chart for the classification process. The construction of formal description in the current study is image grouping (block 200 in FIG. 15A). A decision-theoretic classifier is applied to each image group to estimate which class this group belongs to. The classifier works on multiple-parameter descriptors: the shape of the images and the diameters of images. Decisions are made by priori knowledge, that is, groups with 'ring' shapes are classified to glomeruli (block 300 in FIG. 15 identifying the first decision block); and groups without 'ring' shapes are categorized to sclerous glomeruli, blood vessels, or tubules based on the statistical value of their diameters after the diameters are calculated (blocks 400, 500 and 600 in FIG. 15A). Therefore, after the accomplishment of image classification, each ROI is categorized to one of the three main microstructures in the human kidney: glomeruli, blood vessels, and tubules. T1 and T2 in FIG. 15A are thresholds derived from statistical diameter values to distinguish group classes, and HIST refers to a histogram, such as the histogram shown by FIG. 15B. As indicated above, FIG. 15B is an exemplary histogram depicting the size distribution of kidney structures (glomeruli, blood vessels, and tubules).

Figure 16A:
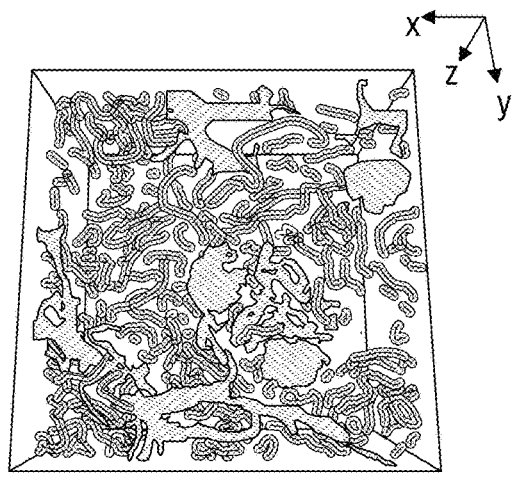
FIG. 16A shows human kidney image classification and automated tubule analysis using KVAS according to the present disclosure.
Figure 16B:
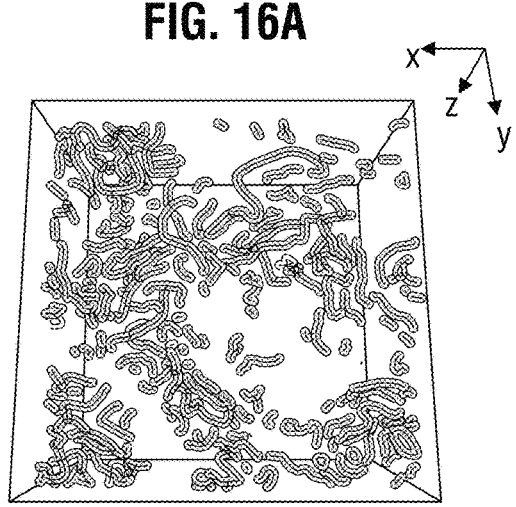
FIG. 16B illustrates different shading is used to distinguish glomeruli, blood vessels, and tubules—to yield a segmented OCT showing tubular structures only (i.e., tubules)
Figure 16C:
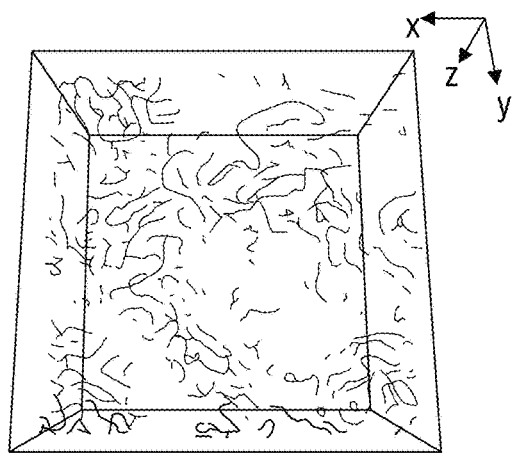
FIG. 16C illustrates 3D skeletonization of segmented tubules.

FIG. 16A shows human kidney image classification and automated tubule analysis using KVAS according to the present disclosure. Classification of kidney features/structures is color-coded but shown using different shading in gray scale in the figure: wormlike structures (tubules); shading with lines drawn diagonally from top left to bottom right (blood vessels); and shading with lines drawn diagonally from top right to bottom left (glomeruli). That is, in FIG. 16B, different shading is used to distinguish glomeruli, blood vessels, and tubules. All three classes of microstructures are present within this data set. FIG. 16B is an image of segmented OCT showing tubular structures only (i.e., tubules). FIG. 16C illustrates 3D skeletonization of segmented tubules.

FIG. 16A shows the results of the image classification scheme for one representative data set. The three groups of human kidney microstructures are distinguished in FIG. 16A by different shading (different colors can also be used to distinguish the microstructures): wormlike structures (tubules); shading with lines drawn diagonally from top left to bottom right (blood vessels); and shading with lines drawn diagonally from top right to bottom left (glomeruli).

All three classifications are clearly visible in FIG. 16A but it is evident that some structures are mislabeled (such as the adjacent uriniferous tubules near the glomeruli). Since the proximal convoluted tubule is physically attached to the glomerulus, this error in group classification is not unexpected. It might be possible to correct this error by using image opening and structure thinning strategies (erosion & dilation) to further separate segmented features in the data set. But, even with the minor misclassification of the juxtaposed tubules, the tubule diameters and density values will not be affected because the glomerulus and the mislabeled tubule will be removed as shown in FIG. 16B and will not contribute to the calculations (density=tubular voxels/(tubular voxels+parenchymal voxels), where parenchymal voxels are not including glomeruli and vessel groups).

Nonetheless, optimizing the OCT segmentation process will improve image grouping, and thus, the overall classification algorithm. Other more advanced techniques for OCT segmentation, such as marker-controlled watershed segmentation [82] are being studied. Also, it would be useful to employ more advanced image processing methods to improve classification of groups. Increasing the number of parameters to include the boundary curvature for each group (tubules have high surface curvature radially compared to glomeruli) and the degree of skeleton branching (glomeruli skeleton is more highly branched whereas tubule skeleton branching is minimal) that can be used for criterion will allow better group analysis. Ultimately, the best classification criteria will be based empirically upon which parameters provide the best results and improve the accuracy of the algorithm.

After classification, tubular regions will be selected for further analysis (FIG. 16B). Then, 3D skeletonization will be performed on the segmented tubular volume to obtain an interconnected skeleton of the entire tubular network (FIG. 16C). The minimum distance between every skeleton element to the 3D boundary of the tubule surface can be computed automatically for the complete volume to yield a distribution of tubule diameters for the entire 3D tubular network. This approach promises to be more accurate than the 2D boundary computation method from the initial algorithm described above. 3D computation does not restrict the boundary of the group to lie only within the current XZ frame where the primary segmented ROI appears but enables the determination of the diameter along the central axis of the tubule. Furthermore, as automatic image processing for 3D data sets could be time-consuming, graphic processing units (GPUs) can be used to perform parallel computing to accelerate the computational process [83-85].

Aim 3. Derive the diagnostic criteria for assessing transplant kidney function and perform prospective clinical studies to assess the accuracy of predicting post-transplant function using OCT/DOCT by using KVAS.

Methods:

Human patients will be recruited. After informed consent, imaging will be performed on a group of 100 patients clinically indicated to undergo kidney transplantation as the standard of care. Patients will then undergo standard protocol in preparation for surgery. During standard transplantation procedure, the disinfected handheld OCT imaging probe (covered by a sterile sleeve) will be placed on the transplant kidney. OCT imaging will be performed at representative regions in the kidney as described previously in Aim 1. OCT imaging will be performed before and after transplantation of kidney. BUN, serum creatinine, urine pH, urine specific gravity, and volume in urine samples will be taken after transplantation. These measurements will be correlated with optical imaging parameters.

Statistical Plan—Sample Size:

Since this is a pilot study and no previous studies have ever addressed the proposed problem, no sample size or power calculation will be conducted. The co-inventors herein will recruit 100 patients for diagnostic criteria development (Testing Group), and another 100 patients for validation of the criteria (Validation Group). Those numbers will ensure enough power for the statistical analysis. The co-inventors herein will revisit the power calculation when the co-inventors herein have quantitative data from 50 patients. If necessary, the co-inventors herein will adjust the patient numbers in Testing and Validation groups.

Statistical Analysis:

The hypothesis that quantitative OCT imaging parameters are correlated with kidney viability and post-transplant renal function will be statistically tested and validated. Our previous work indicates pre-transplantation morphological parameters are closely related to DGF [7], and renal allograft blood flow has been shown to predict postoperative ATN in 87% of patients [86]. In our study, quantitative OCT/DOCT image parameters will be acquired as described in Aim 2, including: 1) Pre-transplantation morphological parameters (tubular diameter and density); 2) Post-transplantation morphological parameters (tubular diameter and density); and 3) Post-transplantation blood flow.

Those quantitative OCT/DOCT image parameters will be used to model post-transplant renal function using a parametric cure survival model [87]. This model can be considered as a combination of logistic regression model for binary responses (success and failure) and a survival model for time-to-event of interest. In such a model, the co-inventors herein define the event of interest as the transplanted kidneys begin to function after the transplantation, the event time as the time when transplanted kidneys begin to function after the transplantation, and cure if the transplanted kidneys will fail to function (i.e. the event will not happen). Even if most of the patients do not exhibit significant DGF, a normative database for those parameters will be constructed for the first time and serve as the foundation for future larger-scale clinical studies. The feedback from the clinical investigator will help to continuously refine the design of the real-time imaging technology.

The linear predictor from the cure survival model will be performed to classify the patients [88]. There are different ways of classification. In particular, the co-inventors herein will group patients as high- and low-risk of transplantation failure. In this case, receiver operating characteristic (ROC) curve will be used to assess the validity of the classification. Sensitivity, specificity, and diagnostic accuracy of OCT for AKI will be established in human for binary classification. Alternatively, the co-inventors herein will develop a scoring system for describing different grades of acute tubular necrosis (ATN): 1) Normal function; 2) Mild ATN; 3) Moderate ATN; 4) Severe ATN; 5) No function. As there is currently no standard grading system for ATN, the co-inventors herein believe the scoring system based on the clinical and image measurements the co-inventors herein will develop will make a signification contribution.

Prospective Validation:

The established classification rules will be tested and validated on an independent dataset from another 100 patients prospectively. After statistical analysis of approximately 100 donor kidneys (within the first two years of the study) using the algorithms described above, the co-inventors herein will perform prospective analysis to predict post-transplant renal function. Therefore, the prospective studies are planned for the latter two years of the study.

At the end of this project, the co-inventors herein expect that the new quantitative OCT imaging technology (KVAS) for kidney viability assessment will be validated. This technology allows the surgeon to scan different regions of the kidney, display both anatomic and functional images of the kidney, and quantify the parameters (such as tubular diameter, density, and blood flow) in real-time. After scanning the whole kidney, a global average of those quantitative parameters will also be presented to provide the clinician with an overall assessment of kidney status. This technology is uniquely suited for quantitative and reliable imaging of transplant kidney structure and function in transplantation clinics. This unprecedented information will augment the transplant surgeon's capability to assess the viability of the donor kidney and enhance the effectiveness of the treatments. After successful completion of this project, co-inventors plan to move forward to a larger-scale clinical study to further evaluate the efficacy of this technology.

III. Additional Studies and Results

The inventors obtained preliminary data demonstrating the capability of OCT and two-photon microscopy (TPM) on monitoring morphological and functional changes during chronic kidney disease (CKD) progression. The animal models used in the study included a drug-induced CKD model and a spontaneous aging CKD model. For drug-induced CKD, Adriamycin (Doxorubicin) (1.5 mg/kg) was injected into the tail vein of Munich-Wistar rats, and OCT/TPM was used to weekly image kidney morphology/functions up to 8 weeks. For spontaneous aging CKD, adult male Munich-Wistar rats were divided into three groups and imaged by OCT/TPM: young adult rats (age 3-5 months), late middle age (10-12 months), and old rats (age 16-18 months) with n=5-7 for each group.

A. OCT Imaging of CKD

FIG. 17 shows OCT/DOCT imaging showing the blood flow, glomerulus, and tubules in rat kidneys. Cross-sectional OCT/DOCT images of normal (images A and B) and diseased rat kidneys after Adriamycin-induced CKD at week 2

(images C and D) and week 3 (images E and F). Less blood flow inside glomeruli was seen at weeks 2 and 3 after drug induction (images C and E).

That is, FIG. 17 shows representative OCT images of control (A, B) and Adriamycin-induced CKD rats at 2-weeks (C, D) and 3-weeks (E, F) after Adriamycin injection. Images A, C, E show cross-sectional OCT images revealing circular glomerular structure surrounded by the crescent shaped capsular space of Bowman. Various renal micro-structures were seen including uriniferous tubules, glomeruli, and parenchyma. OCT reveals sclerotic glomerulus with shrinkage in capillary tufts (images C&D) compared to the control group (images A&B). The shrinkage of the glomerular capillary flow can be seen in images C and E compared to the control in image A.

FIG. 18 illustrates an upper row of images of the kidney of a control animal for different cross-sections across a single glomerulus ranging from Y=0 μm, Y=15 μm, Y=30 μm, Y=45 μm, Y=60 μm, and Y=75 μm and a lower row of images of the kidney of the glomerulus at Week 8 of a CDK animal at the same cross-sections across a single glomerulus showing that increased Bowman's space and decreased blood flow were seen in the glomerulus of week 8 CDK animal, indicating glomerulosclerosis.

More particularly, FIG. 18 shows cross-sectional OCT/DOCT images revealing renal microanatomy and the spatial location of the DOCT capillary flow signal within the glomerulus. The upper row images are from a control rat kidney and the bottom row images are from an Adriamycin-induced CKD rat kidney after Adriamycin injection for 8 weeks. Sclerotic glomerulus was visualized and distinguished from normal by the irregular distended Bowman's space volume and less visible capillary tuft (low layer images). OCT can visualize the shrinkage of the sclerotic glomerular capillary tufts. The corresponding DOCT images from the same plane depict reduced blood flow clearly (i.e., fewer red/blue color pixels, color-coded in gray scale, in the bottom row images). Similar features have been observed on spontaneous aging CKD as well.

In addition, the inventors developed image processing algorithms according to the present disclosure to quantify morphometric parameters based on OCT images.

FIG. 19A shows an example OCT image of a rat kidney with tubular opening percentage of 29%.

FIG. 19B is an image segmentation algorithm to quantify the opening areas within the ROI (from the surface to 177 μm below the surface).

Figure 19C:
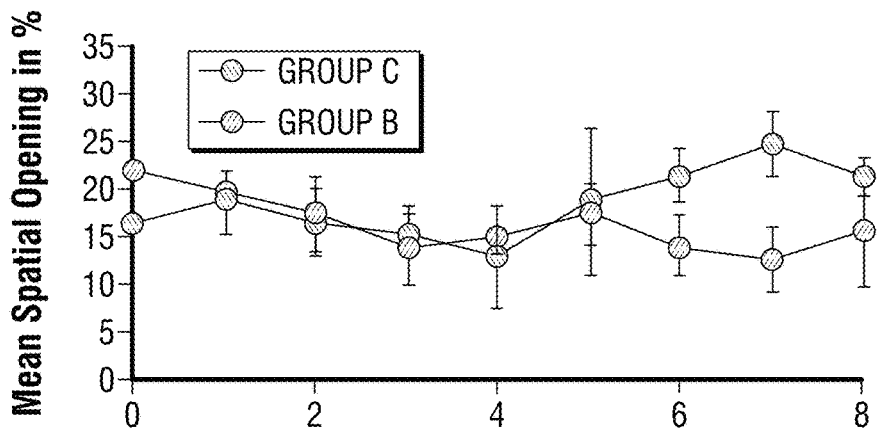
FIG. 19C is a graphical plot of the mean and standard deviation of tubular opening percentage from OCT images at post-Adriamycin injection weeks for 6 month old (group B) and 5 month old rats (group C)

FIG. 19C is a graphical plot of the mean and standard deviation of tubular opening percentage from OCT images at post-Adriamycin injection weeks for 6 (group B) and 5 month old rats (group C).

Figure 19D:
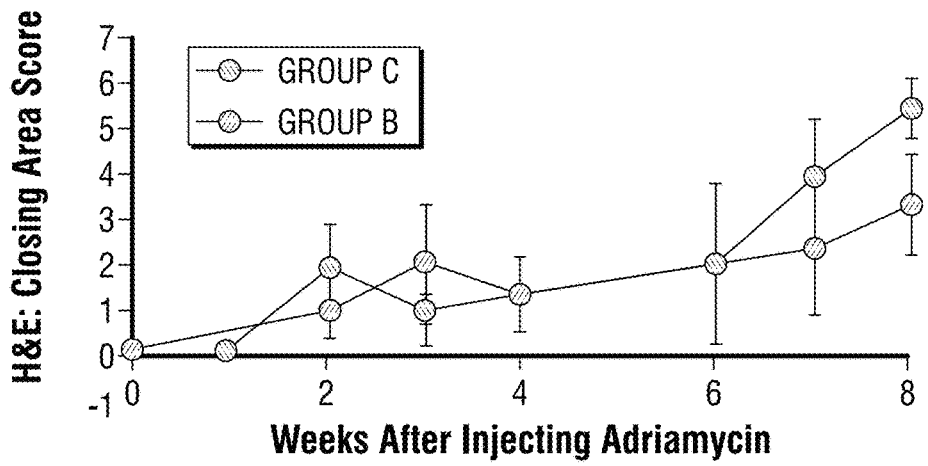
FIG. 19D is a graphical plot of H&E scored closing area as a function of post-Adriamycin injection time.

FIG. 19D is a graphical plot of H & E scored closing area as a function of post-Adriamycin injection time.

Figure 19E:
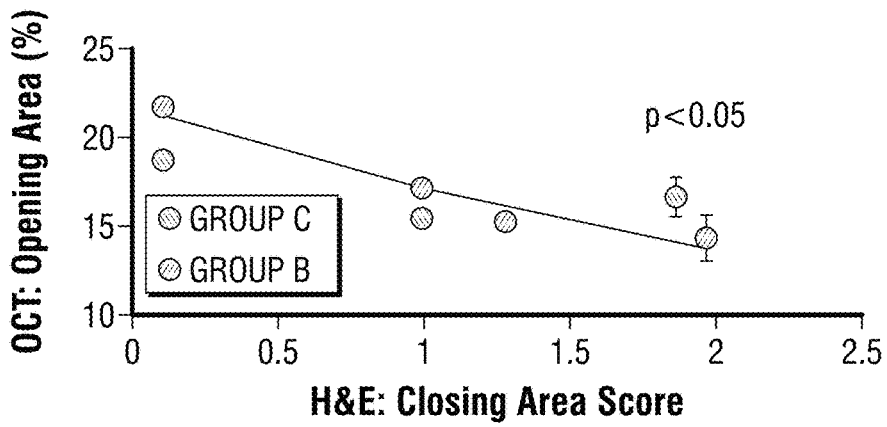
FIG. 19E is a graphical plot of the correlation between quantitative opening area from OCT and H&E scored closing area.

FIG. 19E is a graphical plot of the correlation between quantitative opening area from OCT and H&E scored closing area. Serum creatinine does not show correlation with H&E score or OCT quantitative opening area.

Specifically, they analyzed the percentage of open tubular area within a region of interest (ROI) (FIGS. 19 A & 19B). The OCT images were obtained from 5-10 locations of each kidney. Each location has at least 475 adjacent images acquired. FIG. 19C shows the average results of two groups of Adriamycin-induction CKD rats. Group C is from 5 month old rats and group B is from 6 month old rats.

The result shows both groups have similar trend of declined tubular opening area (indicating tubular density) due to tubular necrosis and interstitial fibrosis within the first 4 weeks following Adriamycin injection. From week 4 to 8 after Adriamycin induction, changes in tubular opening are percentage occurred due to both interstitial fibrosis and tubular dilation. The tubule density due to closing tubule within the first 4 weeks is correlated with histology (FIG. 19D). Urinalysis protein is not associated with Adriamycin induction time. Blood creatinine levels remained less than 2.0 for most of rat except 8 week post-Adriamycin induction rat (blood creatinine level=2.2 mg/dL) in Adriamycin induction model. The results suggest OCT image analysis can provide addition information that might be more sensitive to conventional blood test in determining early kidney dysfunction.

While several embodiments and methodologies of the present disclosure have been described and shown in the drawings, it is not intended that the present disclosure be limited thereto, as it is intended that the present disclosure be as broad in scope as the art will allow and that the specification be read likewise. Therefore, the above description should not be construed as limiting, but merely as exemplifications of particular embodiments and methodologies. Those skilled in the art will envision other modifications within the scope of the claims appended hereto.

REFERENCES CITED

1. *United States Renal Data System Annual Data Report*, (2009).
2. F. Sanfilippo, W. K. Vaughn, E. K. Spees, and B. A. Lucas, *The detrimental effects of delayed graft function in cadaver donor renal transplantation*. Transplantation, 38(6): p. 643-8 (1984).
3. M. Szostek, R. Danielewicz, B. Lagiewska, M. Pacholczyk, Z. Rybicki, G. Michalak, L. Adadynski, J. Walaszewski, and W. Rowinski, *Successful transplantation of kidneys harvested from cadaver donors at 71 to 259 minutes following cardiac arrest*. Transplant Proc, 27(5): p. 2901-2 (1995).
4. J. Light, *Viability testing in the non-heart-beating donor*. Transplant Proc, 32(1): p. 179-81 (2000).
5. A. B. Maunsbach, *The influence of different fixatives and fixation methods on the ultrastructure of rat kidney proximal tubule cells. I. Comparison of different perfusion fixation methods and of glutaraldehyde, formaldehyde and osmium tetroxide fixatives*. J Ultrastruct Res, 15(3): p. 242-82 (1966).
6. P. M. Andrews, *Noninvasive vital microscopy to monitor tubular necrosis of cold-stored kidneys*. Transplantation, 57(8): p. 1143-8 (1994).
7. P. M. Andrews, B. S. Khirabadi, and B. C. Bengs, *Using tandem scanning confocal microscopy to predict the status of donor kidneys*. Nephron, 91(1): p. 148-55 (2002).
8. V. Campo-Ruiz, G. Y. Lauwers, R. R. Anderson, E. Delgado-Baeza, and S. Gonzalez, *Novel virtual biopsy of the kidney with near infrared, reflectance confocal microscopy: a pilot study in vivo and ex vivo*. J Urol, 175(1): p. 327-36 (2006).
9. J. J. Kang, I. Toma, A. Sipos, F. McCulloch, and J. Peti-Peterdi, *Quantitative imaging of basic functions in renal (patho)physiology*. Am J Physiol Renal Physiol, 291(2): p. F495-502 (2006).
10. K. Dunn, R. Sandoval, K. Kelly, P. C. Dagher, G. A. Tanner, S. J. Atkinson, R. L. Bacallao, and B. A. Molitoris, *Functional studies of the kidney of living animals using multicolor two photon microscopy*. Am J Physiol Cell Physiol, 283(3): p. C905-16 (2002).

11. W. Yu, R. M. Sandoval, and B. A. Molitoris, *Rapid determination of renal filtration function using an optical ratiometric imaging approach*. Am J Physiol Renal Physiol, 292(6): p. F1873-80 (2007).

12. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, *Optical coherence tomography*. Science, 254(5035): p. 1178-1181 (1991).

13. J. G. Fujimoto, *Optical coherence tomography for ultrahigh resolution in vivo imaging*. Nature Biotechnology, 21(11): p. 1361-1367 (2003).

14. M. R. Hee, J. A. Izatt, E. A. Swanson, D. Huang, J. S. Schuman, C. P. Lin, C. A. Puliafito, and J. G. Fujimoto, *Optical coherence tomography of the human retina*. Archives of Ophthalmology, 113(3): p. 325-332 (1995).

15. C. A. Puliafito, M. R. Hee, J. S. Schuman, and J. G. Fujimoto, *Optical coherence tomography of ocular diseases* Thorofare, N.J.: Slack Inc. (1996).

16. G. Wollstein, L. A. Paunescu, T. H. Ko, J. G. Fujimoto, A. Kowalevicz, I. Hartl, S. Beaton, H. Ishikawa, C. Mattox, O. Singh, J. Duker, W. Drexler, and J. S. Schuman, *Ultrahigh-resolution optical coherence tomography in glaucoma*. Ophthalmology, 112(2): p. 229-37 (2005).

17. M. Brezinski, *Characterizing arterial plaque with optical coherence tomography*. Current opinion in cardiology, 17(6): p. 648-55 (2002).

18. I. K. Jang, B. Bouma, B. MacNeill, M. Takano, M. Shishkov, N. Iftima, and G. J. Tearney, *In-vivo coronary plaque characteristics in patients with various clinical presentations using Optical Coherence Tomography*. Circulation, 108(17): p. 373-373 (2003).

19. B. E. Bouma, G. J. Tearney, C. C. Compton, and N. S. Nishioka, *High-resolution imaging of the human esophagus and stomach in vivo using optical coherence tomography*. Gastrointestinal Endoscopy, 51: p. 467-74 (2000).

20. M. V. Sivak, Jr., K. Kobayashi, J. A. Izatt, A. M. Rollins, R. Ung-Runyawee, A. Chak, R. C. Wong, G. A. Isenberg, and J. Willis, *High-resolution endoscopic imaging of the GI tract using optical coherence tomography*. Gastrointestinal Endoscopy, 51: p. 474-9 (2000).

21. X. D. Li, S. A. Boppart, J. Van Dam, H. Mashimo, M. Mutinga, W. Drexler, M. Klein, C. Pitris, M. L. Krinsky, M. E. Brezinski, and J. G. Fujimoto, *Optical coherence tomography: advanced technology for the endoscopic imaging of Barrett's esophagus*. Endoscopy, 32(12): p. 921-30 (2000).

22. Y. Chen, A. D. Aguirre, P. L. Hsiung, S. Desai, P. R. Herz, M. Pedrosa, Q. Huang, M. Figueiredo, S. W. Huang, A. Koski, J. M. Schmitt, J. G. Fujimoto, and H. Mashimo, *Ultrahigh resolution optical coherence tomography of Barrett's esophagus: preliminary descriptive clinical study correlating images with histology*. Endoscopy, 39(7): p. 599-605 (2007).

23. J. Welzel, E. Lankenau, R. Birngruber, and R. Engelhardt, *Optical coherence tomography of the human skin*. Journal of the American Academy of Dermatology, 37(6): p. 958-63 (1997).

24. L. L. Otis, M. J. Everett, U. S. Sathyam, and B. W. Colston, Jr., *Optical coherence tomography: a new imaging technology for dentistry*. The Journal of the American Dental Association, 131(4): p. 511-4 (2000).

25. A. V. D'Amico, M. Weinstein, X. Li, J. P. Richie, and J. Fujimoto, *Optical coherence tomography as a method for identifying benign and malignant microscopic structures in the prostate gland*. Urology, 55(5): p. 783-7 (2000).

26. C. Pitris, A. Goodman, S. A. Boppart, J. J. Libus, J. G. Fujimoto, and M. E. Brezinski, *High-resolution imaging of gynecologic neoplasms using optical coherence tomography*. Obstetrics and Gynecology, 93(1): p. 135-9 (1999).

27. G. J. Tearney, S. A. Boppart, B. E. Bouma, M. E. Brezinski, N. J. Weissman, J. F. Southern, and J. G. Fujimoto, *Scanning single-mode fiber optic catheter-endoscope for optical coherence tomography*. Optics Letters, 21(7): p. 543-5 (1996).

28. P. R. Herz, Y. Chen, A. D. Aguirre, J. G. Fujimoto, H. Mashimo, J. Schmitt, A. Koski, J. Goodnow, and C. Petersen, *Ultrahigh resolution optical biopsy with endoscopic optical coherence tomography*. Optics Express, 12(15): p. 3532-3542 (2004).

29. X. Li, C. Chudoba, T. Ko, C. Pitris, and J. G. Fujimoto, *Imaging needle for optical coherence tomography*. Optics Letters, 25(20): p. 1520-2 (2000).

30. Y. Chen, P. M. Andrews, A. D. Aguirre, J. M. Schmitt, and J. G. Fujimoto, *High-resolution three-dimensional optical coherence tomography imaging of kidney microanatomy ex vivo*. J Biomed Opt, 12(3): p. 034008 (2007).

31. P. M. Andrews, Y. Chen, M. L. Onozato, S. W. Huang, D. C. Adler, R. A. Huber, J. Jiang, S. E. Barry, A. E. Cable, and J. G. Fujimoto, *High-resolution optical coherence tomography imaging of the living kidney*. Lab Invest, 88(4): p. 441-449 (2008).

32. J. Wierwille, P. M. Andrews, M. L. Onozato, J. Jiang, A. Cable, and Y. Chen, *In vivo, label-free, three-dimensional quantitative imaging of kidney microcirculation using Doppler optical coherence tomography*. Lab Invest, 91(11): p. 1596-1604 (2011).

33. T. Yamamoto, T. Tada, S. V. Brodsky, H. Tanaka, E. Noiri, F. Kajiya, and M. S. Goligorsky, *Intravital videomicroscopy of peritubular capillaries in renal ischemia*. Am J Physiol Renal Physiol, 282(6): p. F1150-5 (2002).

34. M. Angelescu, T. Kraus, M. Wiesel, O. Hergesell, U. Haberkorn, and E. Klar, *Assessment of renal graft function by perioperative monitoring of cortical microcirculation in kidney transplantation*. Transplantation, 75(8): p. 1190-6 (2003).

35. Y. Ogasawara, K. Takehara, T. Yamamoto, R. Hashimoto, H. Nakamoto, and F. Kajiya, *Quantitative blood velocity mapping in glomerular capillaries by in vivo observation with an intravital videomicroscope*. Methods Inf Med, 39(2): p. 175-8 (2000).

36. H. N. Ibrahim and T. H. Hostetter, *Diabetic nephropathy*. J Am Soc Nephrol, 8(3): p. 487-93 (1997).

37. G. T. O'Bryan and T. H. Hostetter, *The renal hemodynamic basis of diabetic nephropathy*. Semin Nephrol, 17(2): p. 93-100 (1997).

38. I. Ichikawa and A. Fogo, *Focal segmental glomerulosclerosis*. Pediatr Nephrol, 10(3): p. 374-91 (1996).

39. Z. Szabo, J. Xia, W. B. Mathews, and P. R. Brown, *Future direction of renal positron emission tomography*. Semin Nucl Med, 36(1): p. 36-50 (2006).

40. L. Juillard, M. F. Janier, D. Fouque, L. Cinotti, N. Maakel, D. Le Bars, P. Y. Barthez, N. Pozet, and M. Laville, *Dynamic renal blood flow measurement by positron emission tomography in patients with CRF*. Am J Kidney Dis, 40(5): p. 947-54 (2002).

41. N. Kudomi, N. Koivuviita, K. E. Liukko, V. J. Oikonen, T. Tolvanen, H. Iida, R. Tertti, K. Metsarinne, P. Iozzo, and P. Nuutila, *Parametric renal blood flow imaging using [15O]H2O and PET*. Eur J Nucl Med Mol Imaging, 36(4): p. 683-91 (2009).

42. E. U. Nitzsche, Y. Choi, D. Killion, C. K. Hoh, R. A. Hawkins, J. T. Rosenthal, D. B. Buxton, S. C. Huang, M. E. Phelps, and H. R. Schelbert, *Quantification and para-* metric imaging of renal cortical blood flow in vivo based on Patlak graphical analysis. Kidney Int, 44(5): p. 985-96 (1993).
43. H. R. Middlekauff, E. U. Nitzsche, A. H. Nguyen, C. K. Hoh, and G. G. Gibbs, *Modulation of renal cortical blood flow during static exercise in humans.* Circ Res, 80(1): p. 62-8 (1997).
44. N. M. Alpert, C. A. Rabito, D. J. Correia, J. W. Babich, B. H. Littman, R. G. Tompkins, N. T. Rubin, R. H. Rubin, and A. J. Fischman, *Mapping of local renal blood flow with PET and H(2)(15)O.* J Nucl Med, 43(4): p. 470-5 (2002).
45. N. Michoux, X. Montet, A. Pechere, M. K. Ivancevic, P. Y. Martin, A. Keller, D. Didier, F. Terrier, and J. P. Vallee, *Parametric and quantitative analysis of MR renographic curves for assessing the functional behaviour of the kidney.* Eur J Radiol, 54(1): p. 124-35 (2005).
46. J. P. Vallee, F. Lazeyras, H. G. Khan, and F. Terrier, *Absolute renal blood flow quantification by dynamic MRI and Gd-DTPA.* Eur Radiol, 10(8): p. 1245-52 (2000).
47. L. Bokacheva, H. Rusinek, J. L. Zhang, and V. S. Lee, *Assessment of renal function with dynamic contrast-enhanced MR imaging.* Magn Reson Imaging Clin N Am, 16(4): p. 597-611, viii (2008).
48. C. De Bazelaire, N. M. Rofsky, G. Duhamel, M. D. Michaelson, D. George, and D. C. Alsop, *Arterial spin labeling blood flow magnetic resonance imaging for the characterization of metastatic renal cell carcinoma(1).* Acad Radiol, 12(3): p. 347-57 (2005).
49. H. Akinbi, S. Abbasi, P. L. Hilpert, and V. K. Bhutani, *Gastrointestinal and renal blood flow velocity profile in neonates with birth asphyxia.* J Pediatr, 125(4): p. 625-7 (1994).
50. F. van Bel, G. L. Guit, J. Schipper, M. van de Bor, and J. Baan, *Indomethacin-induced changes in renal blood flow velocity waveform in premature infants investigated with color Doppler imaging.* J Pediatr, 118(4 Pt 1): p. 621-6 (1991).
51. S. N. Wong, R. N. Lo, and E. C. Yu, *Renal blood flow pattern by noninvasive Doppler ultrasound in normal children and acute renal failure patients.* J Ultrasound Med, 8(3): p. 135-41 (1989).
52. T. Yura, S. Yuasa, M. Fukunaga, K. F. Badr, and H. Matsuo, *Role for Doppler ultrasound in the assessment of renal circulation: effects of dopamine and dobutamine on renal hemodynamics in humans.* Nephron, 71(2): p. 168-75 (1995).
53. K. Kalantarinia, J. T. Belcik, J. T. Patrie, and K. Wei, *Real-time measurement of renal blood flow in healthy subjects using contrast-enhanced ultrasound.* American Journal of Physiology-Renal Physiology, 297(4): p. F1129-F1134 (2009).
54. D. H. Kay, M. Mazonakis, C. Geddes, and G. Baxter, *Ultrasonic microbubble contrast agents and the transplant kidney.* Clin Radiol, 64(11): p. 1081-7 (2009).
55. P. M. Andrews, W. M. Petroll, H. D. Cavanagh, and J. V. Jester, *Tandem scanning confocal microscopy (TSCM) of normal and ischemic living kidneys.* Am J Anat, 191(1): p. 95-102 (1991).
56. V. Yang, M. Gordon, B. Qi, J. Pekar, S. Lo, E. Seng-Yue, A. Mok, B. Wilson, and I. Vitkin, *High speed, wide velocity dynamic range Doppler optical coherence tomography (Part I): System design, signal processing, and performance.* Opt Express, 11(7): p. 794-809 (2003).
57. S. Yazdanfar, A. M. Rollins, and J. A. Izatt, *Imaging and velocimetry of the human retinal circulation with color Doppler optical coherence tomography.* Opt Lett, 25(19): p. 1448-50 (2000).
58. L. Yu and Z. Chen, *Doppler variance imaging for three-dimensional retina and choroid angiography.* J Biomed Opt, 15(1): p. 016029 (2010).
59. Y. Wang, B. A. Bower, J. A. Izatt, O. Tan, and D. Huang, *Retinal blood flow measurement by circumpapillary Fourier domain Doppler optical coherence tomography.* J Biomed Opt, 13(6): p. 064003 (2008).
60. R. M. Werkmeister, N. Dragostinoff, M. Pircher, E. Gotzinger, C. K. Hitzenberger, R. A. Leitgeb, and L. Schmetterer, *Bidirectional Doppler Fourier-domain optical coherence tomography for measurement of absolute flow velocities in human retinal vessels.* Opt Lett, 33(24): p. 2967-9 (2008).
61. J. Barton, J. A. Izatt, M. D. Kulkarni, S. Yazdanfar, and A. J. Welch, *Three-dimensional reconstruction of blood vessels from in vivo color Doppler optical coherence tomography images.* Dermatology, 198(4): p. 355-61 (1999).
62. Y. Zhao, Z. Chen, C. Saxer, Q. Shen, S. Xiang, J. F. de Boer, and J. S. Nelson, *Doppler standard deviation imaging for clinical monitoring of in vivo human skin blood flow.* Opt Lett, 25(18): p. 1358-60 (2000).
63. H. Li, B. A. Standish, A. Mariampillai, N. R. Munce, Y. Mao, S. Chiu, N. E. Marcon, B. C. Wilson, A. Vitkin, and V. X. D. Yang, *Feasibility of interstitial Doppler optical coherence tomography for in vivo detection of microvascular changes during photodynamic therapy.* Lasers Surg Med, 38(8): p. 754-61 (2006).
64. V. X. D. Yang, S. J. Tang, M. L. Gordon, B. Qi, G. Gardiner, M. Cirocco, P. Kortan, G. B. Haber, G. Kandel, I. A. Vitkin, B. C. Wilson, and N. E. Marcon, *Endoscopic Doppler optical coherence tomography in the human GI tract: initial experience.* Gastrointest Endosc, 61(7): p. 879-90 (2005).
65. W. M. Stahl, *Effect of Mannitol on the Kidney: Changes in Intrarenal Hemodynamics.* N Engl J Med, 272: p. 382-6 (1965).
66. K. E. Lindstrom, L. Ronnstedt, G. Jaremko, and B. Haraldsson, *Physiological and morphological effects of perfusing isolated rat kidneys with hyperosmolal mannitol solutions.* Acta Physiol Scand, 166(3): p. 231-8 (1999).
67. R. Behnia, E. Koushanpour, and E. A. Brunner, *Effects of hyperosmotic mannitol infusion on hemodynamics of dog kidney.* Anesth Analg, 82(5): p. 902-8 (1996).
68. X. Deng, W. J. Welch, and C. S. Wilcox, *Role of nitric oxide in short-term and prolonged effects of angiotensin II on renal hemodynamics.* Hypertension, 27(5): p. 1173-9 (1996).
69. L. Ekelund and J. Gothlin, *Effect of angiotensin on normal renal circulation determined by angiography and a dye dilution technique.* Acta Radiol Diagn (Stockh), 18(1): p. 39-48 (1977).
70. J. H. Gothlin, J. Krakenes, and S. Tvete, *The effects of angiotensin on the diagnostics and haemodynamics in renal angiography.* Eur J Radiol, 3(4): p. 328-30 (1983).
71. J. E. Hall and J. P. Granger, *Renal hemodynamic actions of angiotensin II: interaction with tubuloglomerular feedback.* Am J Physiol, 245(2): p. R166-73 (1983).
72. K. M. Denton, W. P. Anderson, and R. Sinniah, *Effects of angiotensin II on regional afferent and efferent arteriole dimensions and the glomerular pole.* Am J Physiol Regul Integr Comp Physiol, 279(2): p. R629-38 (2000).

73. V. J. Srinivasan, S. Sakadzic, I. Gorczynska, S. Ruvinskaya, W. Wu, J. G. Fujimoto, and D. A. Boas, *Quantitative cerebral blood flow with optical coherence tomography*. Opt Express, 18(3): p. 2477-94 (2010).

74. Q. Li, M. L. Onozato, P. M. Andrews, C. W. Chen, A. Paek, R. Naphas, S. Yuan, J. Jiang, A. Cable, and Y. Chen, *Automated quantification of microstructural dimensions of the human kidney using optical coherence tomography (OCT)*. Opt Express, 17(18): p. 16000-16 (2009).

75. M. L. Onozato, P. M. Andrews, Q. Li, J. Jiang, A. Cable, and Y. Chen, *Optical coherence tomography of human kidney*. J Urol, 183(5): p. 2090-4 (2010).

76. V. Jayaraman, J. Jiang, H. Li, P. J. S. Heim, G. D. Cole, B. Potsaid, J. G. Fujimoto, and A. Cable, *OCT Imaging up to 760 kHz Axial Scan Rate using Single-Mode 1310 nm MEMS-Tunable VCSELs with >100nm Tuning Range*, in Conference on Lasers and Electro-Optics: Applications and Technology 2011, Optical Society of America: Baltimore, Md. p. PDPB2.

77. A. Agrawal, M. Connors, A. Beylin, C. P. Liang, D. Barton, Y. Chen, R. A. Drezek, and T. J. Pfefer, *Characterizing the point spread function of retinal OCT devices with a model eye-based phantom*. Biomed Opt Express, 3(5): p. 1116-26 (2012).

78. A. Ahmad, S. G. Adie, E. J. Chaney, U. Sharma, and S. A. Boppart, *Cross-correlation-based image acquisition technique for manually-scanned optical coherence tomography*. Opt Express, 17(10): p. 8125-36 (2009).

79. P. M. Andrews and S. B. Bates, *Improving Euro-Collins flushing solution's ability to protect kidneys from normothermic ischemia*. Miner Electrolyte Metab, 11(5): p. 309-13 (1985).

80. P. M. Andrews and S. B. Bates, *Dietary protein prior to renal ischemia dramatically affects postischemic kidney function*. Kidney Int, 30(3): p. 299-303 (1986).

81. C. W. Chen, M. W. Betz, J. P. Fisher, A. Paek, and Y. Chen, *Macroporous hydrogel scaffolds and their characterization by optical coherence tomography*. Tissue Engineering: Part C, 17: p. 101-112 (2011).

82. X. Qi, Y. S. Pan, Z. L. Hu, W. Kang, J. E. Willis, K. Olowe, M. V. Sivak, and A. M. Rollins, *Automated quantification of colonic crypt morphology using integrated microscopy and optical coherence tomography*. Journal of Biomedical Optics, 13(5): p.-(2008).

83. K. Zhang and J. U. Kang, *Real-time intraoperative 4D full-range FD-OCT based on the dual graphics processing units architecture for microsurgery guidance*. Biomed Opt Express, 2(4): p. 764-70 (2011).

84. K. Zhang and J. U. Kang, *Graphics processing unit accelerated non-uniform fast Fourier transform for ultrahigh-speed, real-time Fourier-domain OCT*. Opt Express, 18(22): p. 23472-87 (2011).

85. K. Zhang and J. U. Kang, *Real-time 4D signal processing and visualization using graphics processing unit on a regular nonlinear-k Fourier-domain OCT system*. Opt Express, 18(11): p. 11772-84 (2011).

86. C. B. Anderson and E. E. Etheredge, *Human renal allograft blood flow and early renal function*. Ann Surg, 186(5): p. 564-7 (1977).

87. H. B. Fang, G. Li, and J. Sun, *Maximum likelihood estimation in a semiparametric proportional hazards cure model*. Scandinavian Journal of Statistics, 32: p. 59-75 (2005).

88. Y. Chen, A. D. Aguirre, P. Hsiung, S. W. Huang, H. Mashimo, J. M. Schmitt, and J. G. Fujimoto, *Effects of Axial Resolution Improvement on Optical Coherence Tomography (OCT) Imaging of Gastrointestinal Tissues*. Optics Express, 16: p. 2469-2485 (2008).

89. P. M. Andrews and K. R. Porter, *A scanning electron microscopic study of the nephron*. Am J Anat, 140(1): p. 81-115 (1974).

The invention claimed is:

1. A system of non-invasive assessment of a transplant or donor kidney, said system comprising an optical device for imaging the donor kidney in vivo and generating at least one image; and
at least one processor configured for receiving the at least one image from the optical device, and further configured for executing a set of instructions corresponding to an algorithm for processing the at least one image and determining at least one characteristic corresponding to the viability of the donor kidney, wherein said at least one characteristic corresponds to at least one tubular diameter of at least one kidney microstructure, and wherein the processor further predicts the donor kidney's post-transplant outcome based on the characteristic.

2. The system according to claim 1, wherein the system determines at least one characteristic corresponding to the viability of the donor kidney in real-time.

3. The system according to claim 1, wherein the optical device is a handheld optical coherence tomography imaging device.

4. The system according to claim 1, wherein another of the at least one characteristic corresponds to at least one tubular density of the at least one kidney microstructure.

5. The system according to claim 1, wherein the at least one characteristic is indicative of the donor kidney's functions.

6. The system according to claim 1, wherein the optical device is configured for surveying the entire surface of the donor kidney.

7. The system according to claim 1, wherein the algorithm segments and quantifies the diameter and/or density of the donor kidney's microstructures and blood flows.

8. The system according to claim 1, further comprising a display for displaying quantitative values corresponding to the donor kidney determined by the algorithm.

9. The system according to claim 8, wherein the quantitative values are displayed by the display in real-time.

10. A method for non-invasive assessment of a transplant or donor kidney, said method comprising:
imaging the donor kidney in vivo and generating at least one image by an optical device;
processing, by at least one processor, the at least one image;
determining, by executing a set of instructions on the processor corresponding to an algorithm, at least one characteristic corresponding to the viability of the donor kidney, wherein said at last one characteristic corresponds to at least one tubular diameter of at least one kidney microstructure; and
predicting, based on the characteristic, the donor kidney's post-transplant outcome.

11. The method according to claim 10, wherein the determining step determines the at least one characteristic corresponding to the viability of the donor kidney in real-time.

12. The method according to claim 10, wherein the optical device is a handheld optical coherence tomography imaging device.

13. The method according to claim 10, wherein another of the at least one characteristic corresponds to at least one tubular density of the at least one kidney microstructure.

14. The method according to claim 10, wherein the at least one characteristic is indicative of the donor kidney's functions.

15. The method according to claim 10, wherein the optical device is configured for obtaining data corresponding to the superficial glomeruli of the donor kidney.

16. The method according to claim 10, wherein the processing step comprises segmenting and quantifying the diameter and/or density of the donor kidney's microstructures and blood flows.

17. The method according to claim 10, further comprising displaying quantitative values corresponding to the donor kidney.

18. The method according to claim 17, wherein the quantitative values are displayed by a display in real-time.

19. A computer-readable medium storing a set of instructions configured for being executed by at least one processor for performing a method for non-invasive assessment of a transplant or donor kidney, said method comprising:
Imaging the donor kidney in vivo and generating at least one image by an optical device;
processing the at least one image
determining at least one characteristic corresponding to the viability of the donor kidney, wherein said at least one characteristic corresponds to at least one tubular diameter of at least one kidney microstructure; and
predicting the donor kidney's post-transplant outcome based on the characteristic.

* * * * *